(12) United States Patent
Flaherty et al.

(10) Patent No.: US 10,070,793 B2
(45) Date of Patent: Sep. 11, 2018

(54) ABLATION AND TEMPERATURE MEASUREMENT DEVICES

(75) Inventors: J. Christopher Flaherty, Auburndale, FL (US); John T. Garibotto, Marblehead, MA (US); R. Maxwell Flaherty, Auburndale, FL (US); William J. Gorman, South Hamilton, MA (US)

(73) Assignee: Securus Medical Group, Inc., Cleveland, OH (US)

( * ) Notice: Subject to any disclaimer, the term of this patent is extended or adjusted under 35 U.S.C. 154(b) by 226 days.

(21) Appl. No.: 13/988,637

(22) PCT Filed: Nov. 22, 2011

(86) PCT No.: PCT/US2011/061802
§ 371 (c)(1),
(2), (4) Date: Sep. 26, 2013

(87) PCT Pub. No.: WO2012/071388
PCT Pub. Date: May 31, 2012

(65) Prior Publication Data
US 2014/0012155 A1    Jan. 9, 2014

Related U.S. Application Data

(60) Provisional application No. 61/417,416, filed on Nov. 27, 2010.

(51) Int. Cl.
*A61B 5/01* (2006.01)
*A61B 18/14* (2006.01)
(Continued)

(52) U.S. Cl.
CPC ............ *A61B 5/015* (2013.01); *A61B 5/0086* (2013.01); *A61B 5/6853* (2013.01);
(Continued)

(58) Field of Classification Search
CPC ..... A61B 5/015; A61B 5/0059; A61B 5/0062; A61B 5/0068; A61B 5/0075;
(Continued)

(56) References Cited

U.S. PATENT DOCUMENTS

| 4,648,892 A | 3/1987 | Kittrell et al. |
| 4,953,539 A | 9/1990 | Nakamura et al. |

(Continued)

FOREIGN PATENT DOCUMENTS

| CN | 1888813 | 11/2010 |
| EP | 1280452 | 2/2003 |

(Continued)

OTHER PUBLICATIONS

Internet Archive, RP Photonics, "Encyclopedia of Laser Physics and Technology" Superluminescent Sources, Apr. 20, 2009. Retrieved from <https://web.archive.org/web/20090420055236/http://www.rp-photonics.com/superluminescent_sources.html> on Jul. 23, 2015.*

(Continued)

*Primary Examiner* — David J McCrosky
(74) *Attorney, Agent, or Firm* — Faegre Baker Daniels LLP

(57) ABSTRACT

A temperature measurement probe for a patient is provided. The probe includes a sensor assembly and produces a temperature map comprising temperature information for multiple patient locations.

31 Claims, 21 Drawing Sheets

(51) Int. Cl.
*A61B 5/00* (2006.01)
*A61B 18/18* (2006.01)
*A61B 18/20* (2006.01)
*A61B 18/00* (2006.01)
*A61B 18/02* (2006.01)
*A61B 90/00* (2016.01)

(52) U.S. Cl.
CPC ...... *A61B 18/1492* (2013.01); *A61B 18/1815* (2013.01); *A61B 18/20* (2013.01); *A61B 90/39* (2016.02); *A61B 2018/00357* (2013.01); *A61B 2018/00577* (2013.01); *A61B 2018/00642* (2013.01); *A61B 2018/00702* (2013.01); *A61B 2018/00815* (2013.01); *A61B 2018/00821* (2013.01); *A61B 2018/0212* (2013.01); *A61B 2090/3784* (2016.02)

(58) Field of Classification Search
CPC ... A61B 5/0082; A61B 5/0084; A61B 5/0086; A61B 2017/00084; A61B 2017/00097; A61B 2017/00101; A61B 2017/00053; A61B 2017/00057; A61B 2017/00061; G02B 23/2423; G02B 23/2476
USPC ......... 600/474, 478, 549; 374/131, E13.002, 374/E13.003
See application file for complete search history.

(56) References Cited

U.S. PATENT DOCUMENTS

| | | | |
|---|---|---|---|
| 4,973,848 A | 11/1990 | Kolobanov et al. | |
| 5,380,317 A | 1/1995 | Everett et al. | |
| 5,460,182 A | 10/1995 | Goodman et al. | |
| 5,547,455 A | 8/1996 | McKenna et al. | |
| 5,647,368 A | 7/1997 | Zeng et al. | |
| 5,649,924 A | 7/1997 | Everett et al. | |
| 5,688,267 A | 11/1997 | Panescu et al. | |
| 5,711,755 A * | 1/1998 | Bonnell ............. | A61B 1/042 250/353 |
| 5,792,070 A | 8/1998 | Kauphusman et al. | |
| 5,871,449 A | 2/1999 | Brown | |
| 6,011,891 A * | 1/2000 | Katzir ............. | G01J 5/02 374/E13.003 |
| 6,134,003 A | 10/2000 | Tearney et al. | |
| 6,197,022 B1 | 3/2001 | Baker | |
| 6,245,026 B1 | 6/2001 | Campbell et al. | |
| 6,312,408 B1 | 11/2001 | Eggers et al. | |
| 6,370,422 B1 | 4/2002 | Richards-Kortum et al. | |
| 6,501,551 B1 | 12/2002 | Tearney et al. | |
| 6,516,216 B1 | 2/2003 | Fontenot et al. | |
| 6,575,969 B1 | 6/2003 | Rittman, III et al. | |
| 6,579,243 B2 * | 6/2003 | Kokate ............. | A61B 5/015 600/474 |
| 6,584,360 B2 | 6/2003 | Francischelli et al. | |
| 6,620,189 B1 | 9/2003 | Machold et al. | |
| 6,652,452 B1 * | 11/2003 | Seifert ............. | A61B 1/00096 600/140 |
| 6,706,038 B2 | 3/2004 | Francischelli et al. | |
| 6,709,154 B1 | 3/2004 | Janotte | |
| 6,716,178 B1 | 4/2004 | Kilpatrick et al. | |
| 6,740,082 B2 | 5/2004 | Shadduck | |
| 6,821,249 B2 | 11/2004 | Casscells, III et al. | |
| 6,873,868 B2 | 3/2005 | Furnish | |
| 7,062,306 B2 | 6/2006 | Benaron et al. | |
| 7,081,096 B2 | 7/2006 | Brister et al. | |
| 7,130,047 B2 | 10/2006 | Chinnock et al. | |
| 7,150,745 B2 | 12/2006 | Stern et al. | |
| 7,198,635 B2 | 4/2007 | Danek et al. | |
| 7,264,587 B2 | 9/2007 | Chin | |
| 7,429,261 B2 | 9/2008 | Kunis et al. | |
| 8,029,446 B2 * | 10/2011 | Horiike et al. ............. | 600/463 |
| 8,452,383 B2 | 5/2013 | Norris et al. | |
| 8,545,490 B2 | 10/2013 | Mihajlovic et al. | |
| 8,971,997 B2 * | 3/2015 | Oral et al. ............. | 600/473 |
| 9,247,991 B2 | 2/2016 | Norris et al. | |
| 2002/0076178 A1 | 6/2002 | Klocek et al. | |
| 2003/0013936 A1 | 1/2003 | Jackson, III | |
| 2003/0013986 A1 * | 1/2003 | Saadat ............. | A61B 5/015 600/549 |
| 2003/0014098 A1 | 1/2003 | Quijano et al. | |
| 2003/0028114 A1 | 2/2003 | Casscells, III et al. | |
| 2003/0114761 A1 | 6/2003 | Brown | |
| 2003/0199767 A1 * | 10/2003 | Cespedes ............. | A61B 5/01 600/473 |
| 2003/0233033 A1 | 12/2003 | Korotko et al. | |
| 2004/0138656 A1 | 7/2004 | Francischelli et al. | |
| 2005/0107741 A1 | 5/2005 | Willard et al. | |
| 2005/0154262 A1 | 7/2005 | Banik et al. | |
| 2005/0288654 A1 | 12/2005 | Nieman et al. | |
| 2006/0195014 A1 | 8/2006 | Seibel et al. | |
| 2006/0241484 A1 | 10/2006 | Horiike et al. | |
| 2007/0078500 A1 | 4/2007 | Ryan et al. | |
| 2007/0197919 A1 | 8/2007 | Krisch et al. | |
| 2007/0270717 A1 | 11/2007 | Tang et al. | |
| 2009/0163901 A1 | 6/2009 | Fisher et al. | |
| 2009/0264727 A1 | 10/2009 | Markowitz et al. | |
| 2010/0030098 A1 * | 2/2010 | Fojtik ............. | 600/549 |
| 2011/0028788 A1 | 2/2011 | Oral et al. | |
| 2011/0066035 A1 * | 3/2011 | Norris et al. ............. | 600/478 |
| 2011/0270080 A1 | 11/2011 | Crane | |
| 2012/0035603 A1 | 2/2012 | Lenihan | |
| 2012/0071824 A1 | 3/2012 | Chang et al. | |
| 2012/0232534 A1 | 9/2012 | Rink et al. | |
| 2013/0261613 A1 | 10/2013 | Norris et al. | |
| 2014/0081204 A1 | 3/2014 | Cohen et al. | |
| 2014/0114182 A1 | 4/2014 | Petersen et al. | |
| 2014/0142436 A1 | 5/2014 | Hutchins et al. | |
| 2015/0366461 A1 | 12/2015 | Oral et al. | |

FOREIGN PATENT DOCUMENTS

| | | |
|---|---|---|
| EP | 1717620 | 11/2006 |
| JP | H03277343 | 12/1991 |
| JP | 2005270425 | 10/2005 |
| WO | 2009108950 | 9/2009 |
| WO | 2009120694 | 10/2009 |
| WO | 2010090701 | 8/2010 |
| WO | 0180756 | 11/2011 |
| WO | 2012071388 | 5/2012 |
| WO | 2013172974 | 11/2013 |

OTHER PUBLICATIONS

International Search Report dated Aug. 1, 2012, issued in corresponding International Application No. PCT/US2011/061802.
International Search Report dated Apr. 15, 2014, issued in corresponding International Application No. PCT/US2013/076961.
International Search Report and Written Opinion dated Sep. 9, 2015 issued in corresponding International Patent Application No. PCT/US2015/033680.
Japan Office Action and English language summary dated Aug. 2, 2016, issued in corresponding Japan application No. 2013-541013.
Final Office Action dated Aug. 22, 2016 and English language summary issued in corresponding China Application No. 201180066053.8.
Japan Office Action dated Sep. 29, 2015 issued in corresponding Japanese Patent Application No. 2013-54103.
Examination Report dated May 25, 2016 issued in corresponding Australia patent application No. 2011332014.
Japanese Notice of Allowance dated Mar. 14, 2017 issued in corresponding Japanese Application No. 2013-541013.
Extended European Search Report dated Nov. 16, 2016 issued in corresponding European Application No. 11843655.9.
Chinese Reexamination Notice dated May 27, 2017, issued in corresponding Chinese Application No. 201180066053.8, including English-language summary of the claim rejections.

(56) References Cited

OTHER PUBLICATIONS

Canadian Office Action dated Jun. 21, 2017 issued in corresponding Canadian Application No. 2,852,637.

* cited by examiner

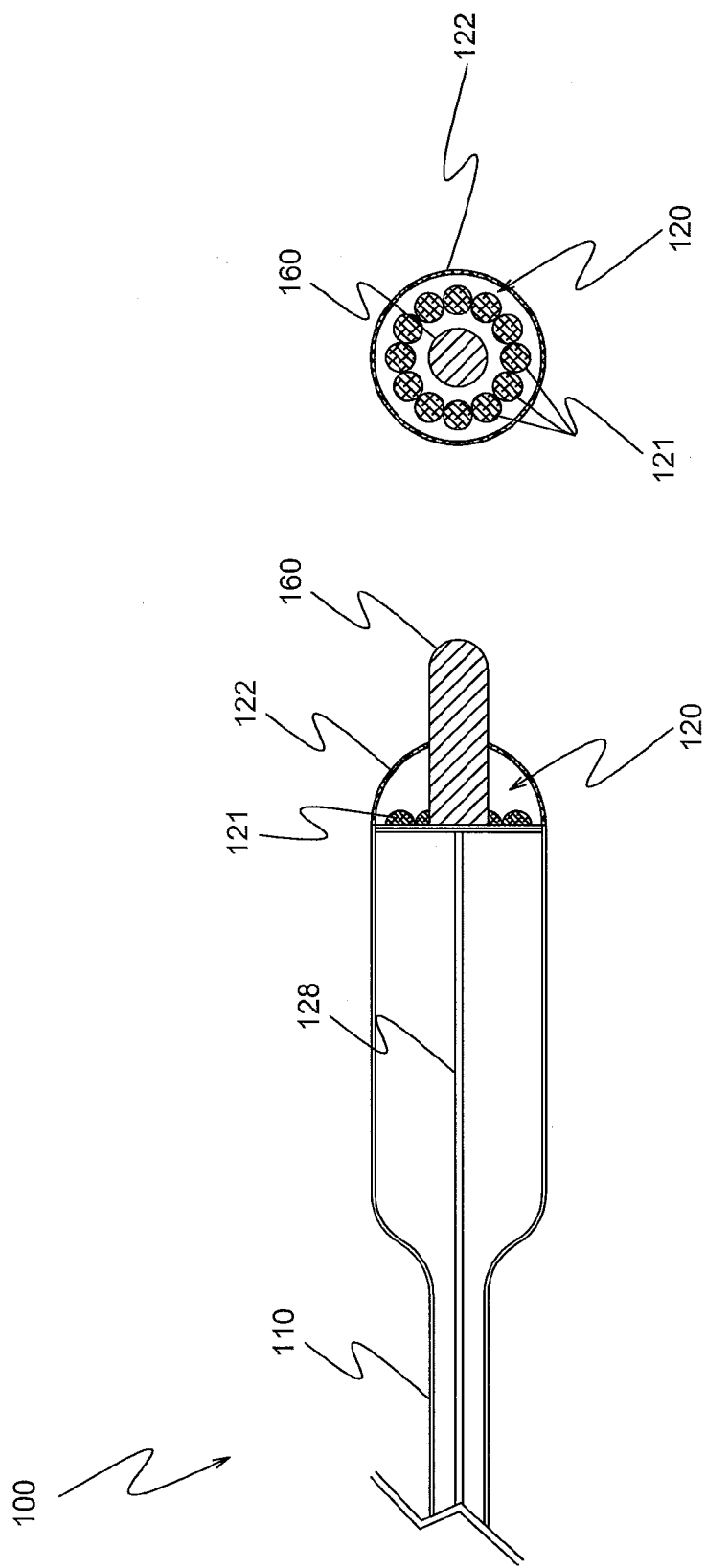

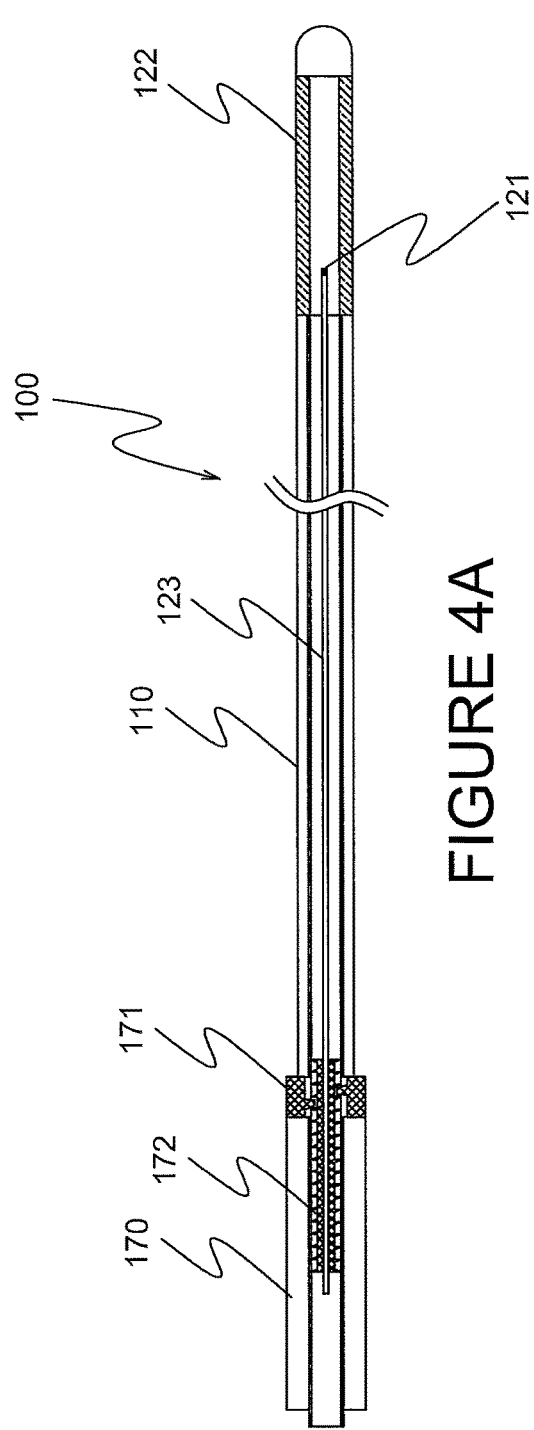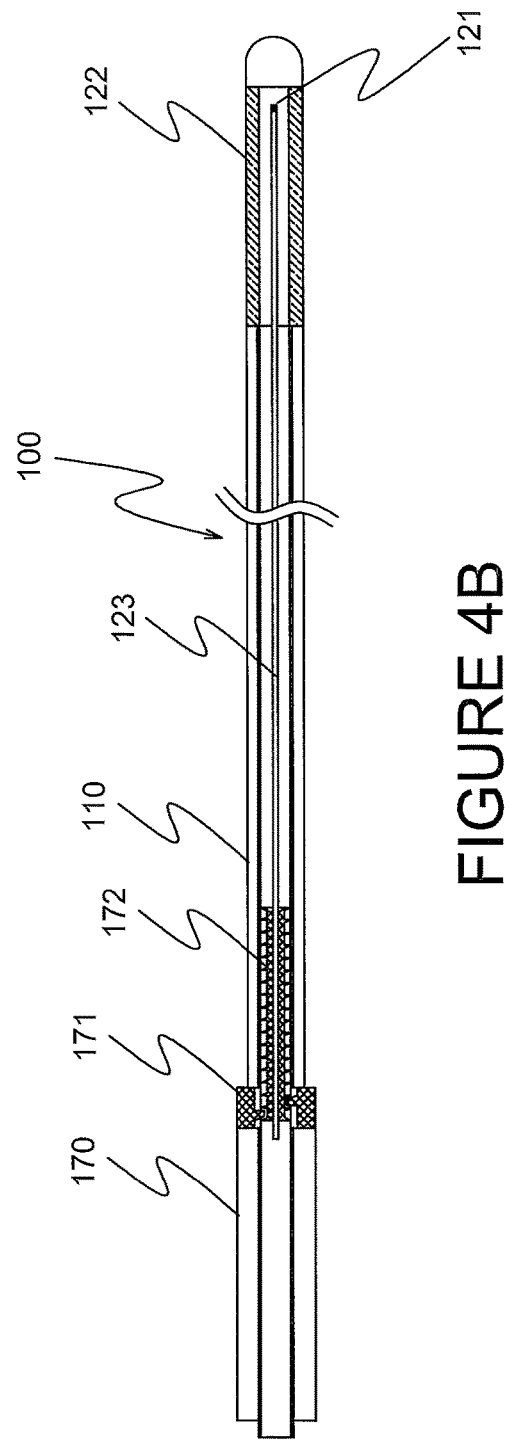

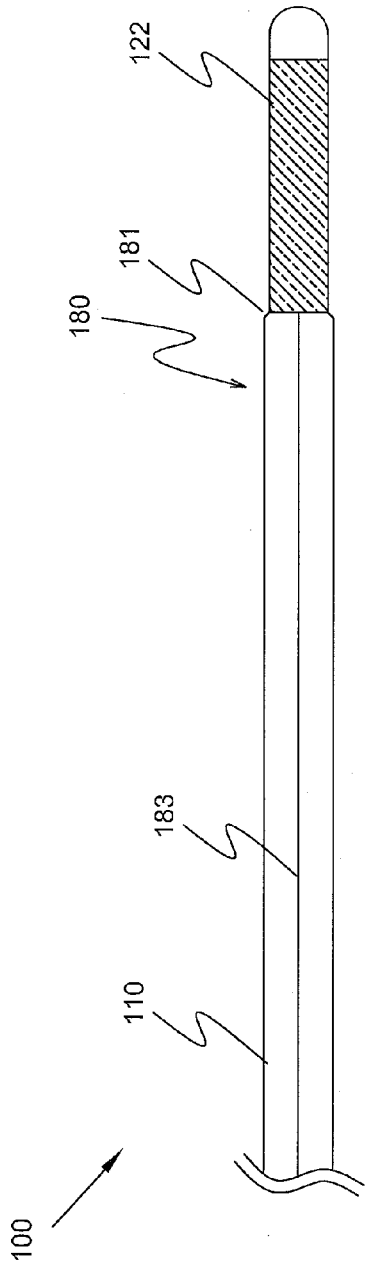
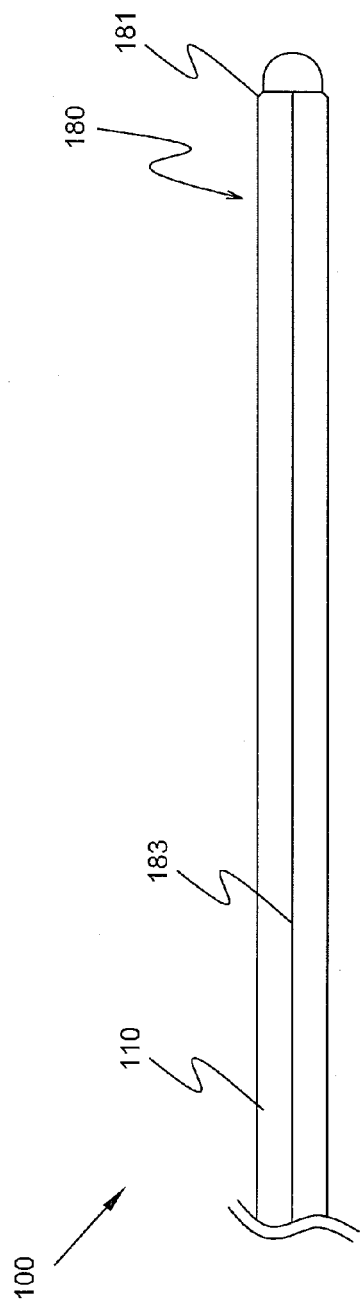

ABLATION AND TEMPERATURE MEASUREMENT DEVICES

RELATED APPLICATIONS

This patent claims priority to U.S. Provisional Application Ser. No. 61/417,416, filed Nov. 27, 2010, to Flaherty, et al, entitled ABLATION AND TEMPERATURE MEASUREMENT DEVICES, and incorporated herein by reference in its entirety.

FIELD

Embodiments relate generally to the field of tissue temperature monitoring, and more particularly, to ablation and temperature measurement devices and systems that monitor tissue temperature during energy delivery.

BACKGROUND

Ablation therapy is a medical procedure where dysfunctional tissue is ablated using various forms of energy, typically in the form of extreme heat or cold. Ablation therapy is utilized to treat tumors in lung, liver, kidney, bone and in other body organs as well as in the treatment of cardiac rhythm conditions such as Atrial Fibrillation. Procedures are typically performed under image guidance, such as X-ray screening, CT scan or ultrasound by an interventional radiologist or cardiac electrophysiologist.

Although ablation treatments are useful, it is difficult to determine with sufficient accuracy the parameters needed for successful treatment. Inexactness in the amount of energy or exposure time of an affected tissue may lead to thermal injury of the adjacent healthy tissues. Catheter ablation of the heart is particularly susceptible to such problems.

Radio-frequency (RF) catheter ablation, for example, is commonly used to treat atrial fibrillation (AF) which is the most common heart arrhythmia leading to hospitalization. A catheter is inserted into a patient's heart or other vessel, and heat is applied to a localized region until the tissue in that region has been sufficiently destroyed to abate the arrhythmia. In other applications, cryoablation has also been used to freeze and destroy local tissue.

The use of extreme energy during cardiac catheter ablation procedures for the treatment of atrial fibrillation is prone to a serious and life-threatening complication known as atrioesophageal fistulas. Atrioesophageal fistula after catheter ablation occurs due to conductive heat transfer to the esophagus that causes transmural tissue necrosis. The close proximity of the esophagus to the posterior wall of the left atrium and the pulmonary veins presents a significant risk of injury to the esophagus during the application of energy to the cardiac tissue. Injury to the esophagus resulting in tissue necrosis can create a delayed opening in the esophageal wall, leading to the formation of a fistula between the atrium and the esophagus. Atrioesophageal fistulas, if not diagnosed and treated promptly, may lead to, infection and sepsis, bleeding, air and particulate-matter emboli, stroke and quite often death.

To date there have been no effective measures to prevent atrioesophageal fistula formation. Various techniques are employed to minimize the likelihood of esophageal injury during percutaneous catheter ablation. Many physicians avoid ablating the posterior wall of the left atrium and pulmonary veins adjacent to the esophagus to reduce the likelihood of injury to the esophagus. Techniques such as altering the lesion set by moving ablation lines away from the areas adjacent to the esophagus add to the difficulty of treating the fibrillation. Physically moving the esophagus away from the heart wall with a luminal transesophageal echo probe is also employed. These techniques are dependent on the specific anatomical location of the esophagus relative to the area being ablated. With no thermal feedback from the esophagus, the physician has no guarantee that energy is not spreading to the esophageal tissue. Atrial fibrillation recurrence rates are thought to be significantly higher when these types of avoidance techniques are employed.

Titration of energy is the most common method employed to minimize risk of esophageal injury during percutaneous catheter ablation. The challenge of this approach is in knowing how much energy can be delivered before injury occurs to the esophagus. Typically the energy that is transferred to the esophagus is measured with a luminal esophageal temperature monitoring catheter. These catheters are placed down the esophagus of the patient and provide a single-point measurement of the temperature at the tip of the catheter. The premise is that this thermal feedback will provide the Electrophysiologist with sufficient information to allow for the proper titration of energy and eliminate risk of injury to the esophagus.

Several challenges limit the effectiveness of luminal esophageal temperature monitoring devices during catheter ablation. Studies employing luminal esophageal temperature monitoring devices reveal that esophageal heating occurs in the range of 0.05-0.1 degrees Celsius (C) per second and that repeated energy applications in the same general area can cause temperature stacking. The physician must position the temperature monitoring device adjacent to the ablation catheter before each pulse of energy. This is very time consuming and difficult to achieve under x-ray guidance. The temperature monitoring catheters are very small in diameter relative to the diameter of the esophagus. It is nearly impossible to position the tip of the temperature probe against the esophageal wall that is adjacent to the area of the heart wall being ablated. Furthermore, the temperature-monitoring catheters are not designed to be torqued or deflected toward the esophageal wall and cannot be positioned precisely within the lumen. A recent study showed that over 6% of patients exhibited evidence of esophageal ulceration after catheter ablation when currently available luminal temperature monitoring products were used and many cases of atrioesophageal fistulas have been documented despite the use of luminal esophageal temperature monitoring devices.

As catheter ablation for the treatment of Atrial Fibrillation expands beyond the premier academic institutions and into the mainstream, the limitations of today's available options for protecting against esophageal injury will become more evident. More physicians will be forced to make the trade-off between sufficient ablation and the potential for damage to the patient's esophagus. In addition to the complications related to esophageal injury, the lack of adequate feedback will result in longer procedure times, excess radiation exposure, and increased arrhythmia recurrence rates.

There is a clear need for improved devices, systems and methods to monitor temperature while actively ablating target tissue in order to achieve the desired clinical outcome without risk of injury to the surrounding healthy tissues.

SUMMARY

According to a first aspect, a temperature measurement probe for a patient is provided including an elongate member and a sensor assembly. The elongate member includes a proximal portion and a distal portion. The probe produces a temperature map comprising temperature information for multiple patient locations. The probe may be side viewing, producing a temperature map for tissue relatively orthogonal to the elongate member distal portion, such as luminal wall tissue of a body lumen such as the esophagus. Alternatively or additionally, the probe may be forward looking, producing a temperature map of tissue that is positioned distal to the distal end of the elongate member.

The elongate member distal portion may be configured for insertion within the body of the patient, such as a patient lumen such as an insertion into the esophagus of a patient during a cardiac ablation procedure. The elongate member proximal portion may comprise a connector such as an electrical connector and/or a fiber optic connector. The elongate member may comprise a thermos construction along at least a portion of its length, such as to minimize the effects of stray infrared radiation not emanating from the multiple patient locations.

The sensor assembly may comprise a non-contact sensor assembly constructed and arranged to measure temperature without making physical contact with the multiple patient locations. The sensor assembly may be configured to be side viewing and/or forward viewing. The sensor assembly may comprise a sensor type selected from the group consisting of: infrared detector or other infrared sensor such as a passive or active infrared sensor; thermocouple, thermopile such as a bolometer, thermister, thermochromic element, pyrometer, liquid crystal such as thermotropic liquid crystals; and combinations of these. The sensor assembly may be configured to detect a non-temperature change, such as a non-temperature change in the multiple tissue locations that can be correlated to an absolute temperature or a relative temperature (e.g. a temperature change). Typical detected non-temperature tissue changes include but are not limited to: color changes; cellular structure changes such as cellular wall expansion; conductivity changes; density changes; and combinations of these. The sensor assembly may be constructed and arranged to detect one or more substances produced by tissue, such a sensor configured to detect the substance through monitoring of one or more of: a color change; detection of the produced substance; detection of a substance produced during cell death; detection of a substance produced during cell damage; detection of an emitted gas; and detection of smoke.

The sensor assembly may include an array of sensors such as an array of passive and/or active infrared sensors. At least a portion of the sensor assembly may be included in the distal portion of the elongate member in relative proximity to the tissue to be measured, such as a sensor assembly comprising a rotating mirror. Alternatively or additionally, at least a portion of the sensor assembly may be located in a more proximal location, such as in the proximal portion of the elongate member, in a handle of the probe, and/or in a separate device that is electrically or optically coupled to the probe. In one embodiment, the sensor assembly includes infrared light detectors that receive infrared radiation that is directed proximally from the elongate member distal portion by a series of lenses and mirrors.

At least a portion of the sensor assembly may be rotated, such as a continuous 360° rotation to measure a full circumferential wall portion of luminal tissue. Partial rotations may be performed such as rotations of at least 90°; at least 180°; no more than 180'; and combinations of these. Rotations may be back and forth in a reciprocating motion (e.g. clockwise followed by counter clockwise rotations). At least a portion of the sensor assembly may be moved axially, such as to translate in a reciprocating repetitive periodic back and forth motion, and the received information combined such as to produce a temperature map of a particular length of tissue that is longer than the sensor assembly. In one embodiment, at least a mirror and a fiber optic are translated in a reciprocating motion. In one embodiment, the sensor assembly is configured to measure the temperature of one patient location at a time. In this configuration, at least a portion of the sensor, such as a mirror, may be configured to rotate and/or translate to gather temperature information from multiple patient locations. Alternatively or additionally, a lens may be configured to move or change shape to gather the multiple patient location temperature information. Alternatively or additionally, the mirror may be configured to change shape to gather the multiple patient location temperature information.

In one embodiment, the probe includes a second sensor assembly, such as a sensor assembly with a different construction than the first sensor assembly. The second sensor assembly may be an array of sensors, such as an array of infrared light detectors or other infrared sensors.

In one embodiment, the sensor assembly comprises an array of sensors, such as an array of spinning sensors configured to rotate at least 90°. The array may be a linear array, such as a linear array with a length of at least 2" or a length of at least 3". The sensor assembly may include a lens, such as a lens configured to focus light such as infrared light energy on the array of sensors.

In one embodiment, at least a portion of the sensor assembly is positioned in the elongate member distal portion. This sensor array portion may be configured to spin and/or translate. This sensor array portion may include an integrated circuit, such as an integrated circuit including components selected from the group consisting of: multiplexing circuitry components; infrared detectors; rotational movement encoding components; translational movement encoding components; and combinations of these. The sensor array portion may include a lens, such as an infrared transparent lens. The sensor assembly may comprise a transmission conduit traveling from the sensor assembly portion to the elongate member proximal portion. The transmission conduit may be configured to transmit energy and/or data, and may include one or more optical fibers and/or one or more electrical wires.

In one embodiment, at least a portion of the sensor assembly is not positioned in the elongate member distal portion, such as a sensor assembly portion located in the elongate member proximal portion and/or proximal to the elongate member, such as in a separate device. In this embodiment, one or more lenses may be positioned in the elongate member distal portion, such as with an orientation towards tissue whose temperature is to be measured. A transmission conduit may be positioned between the elongate tube distal portion and the sensor assembly portion, such as a transmission conduit including a hollow tube with a lens and/or mirror positioned at or proximate to its distal end. The transmission conduit may be a solid cylinder, such as a cylinder comprising a single fiber or a bundle of fibers. The transmission conduit may be flexible, and it may be configured to rotate and/or translate. A probe with at least a sensor assembly portion not positioned in the elongate tube distal portion may include one or more mirrors constructed and arranged to deflect radiation such as infrared radiation toward the proximal portion of the elongate tube. The mirror may be constructed and arranged to move, such as to rotate and/or translate.

The sensor assembly may include at least one optical fiber, such as a single infrared transparent fiber, or multiple fibers such as multiple infrared fibers in a coherent or non-coherent bundle. Fibers may be constructed of material selected from the group consisting of: germanium; arsenic; selenium; sulfur; tellurium; silver halide; or other materials knows to offer little or no impedance to transmission of infrared light.

The multiple patient locations may comprise a continuous area of tissue surface, or multiple areas such as multiple discrete points. The multiple patient locations may comprise a relatively uni-planar surface (e.g. a relatively flat surface), or it may comprise a multi-planar surface such as a round surface such as the luminal wall of the esophagus or a surface with numerous bumps, ridges, grooves and/or walls, such as the topography inside the lung.

The probe may include a membrane, such as a membrane surrounding at least a portion of the sensor assembly. One or more sensors may be positioned on the membrane, and the membrane may be inflatable. The membrane may comprise the sensor.

The probe may include or otherwise be electronically attachable to a display unit used to display the temperature information, as well as one or more other user output components such as audible transducers, tactile transducers, and other visible transducers such as LEDs and alphanumeric displays. The probe may include signal processing means such as to convert temperature information to color maps such as color maps representing different temperature through differences in color, shade, hue, boldness of text, text font, font type, font size, and the like. Signal processing may mathematically process the temperature information such as to determine maximums, averages, integrations of time at temperature, and the like. The probe may include zooming and panning functions such as automatic zooming and panning functions. In one embodiment, the temperature map provided is zoomed (in or out) or panned based on temperature information shown on this display or information outside of the temperature map that is currently being displayed. The probe may include a feedback circuit used to modify a probe component such as a display or a tissue temperature modifying assembly, or another component such as an energy delivery unit. The display may include the energy delivery unit, and the display may be configured to provide both tissue temperature information and energy delivery information.

An attached display may provide temperature and other information in one or more forms. Temperature information may be displayed in non-numeric forms, such as by displaying temperature level information as represented by one or more of: color; shade; hue; saturation; and brightness. Additionally or alternatively, numeric temperature information may be included, such as information representing current temperature; an average of temperature over time; peak or maximum temperature over time; a representation of historic temperature information; and combinations of these. The display may be configured to allow an operator to adjust a domain of values of the displayed temperature map, such as to correlate a display property such as color to a particular temperature or temperature range. Temperature information can be displayed on a representation of tissue being measured, such as an actual image or artistic rendering of the esophagus when the multiple patient locations comprise locations within the patient's esophagus. Other information may be provided on the display, such as information selected from the group consisting of: a timestamp; a patient ID; a clinician ID; a location such as a location where the procedure was performed; information about the anatomical location of the multiple patient locations; EKG information; energy delivered information; patient physiologic information; and combinations thereof. A user interface may be included, such as to allow an operator to adjust a temperature range, or a correlation of colors to a temperature map. A user interface may be configured to allow an operator to adjust a focus, such as the focus of at least a portion of the probe onto tissue, such as to collect infrared light in a focused manner.

The probe may include an alert element, such as an alert element with adjustable alert parameters. The alert may be activated based on one or more of: information included in the currently provided temperature map; cumulative temperature information collected over time; and combinations of these. The alert may comprise an element selected from the group consisting of: an audible transducer; a visual transducer; a tactile transducer; and combinations of these.

The probe may include a malleable member, such as a malleable member included along at least a portion of the length of the elongate member and configured to allow an operator to plastically deform the elongate member to a desired two or three dimensional shape.

The probe may include one or more lumens, such as one or more lumens extending from the elongate member proximal end or other proximal portion to the elongate member distal end or other distal portion. The one or more lumens may be configured as an inflation lumen, such as to inflate a balloon or other expandable device positioned on or in the elongate member, or the one or more lumens may be configured as a fluid delivery lumen such as to deliver one or more cooling or other fluids to the elongate member distal portion or tissue proximate the elongate member distal portion.

The probe may include one or more cleaning elements, such as an element used to wash or wipe debris from one or more lenses of the probe. The cleaning element may comprise a wiper, such as a wiper configured to move across one or more portions of the sensor assembly, such as across a lens of the sensor assembly. The cleaning element may be constructed and arranged to move in a back and forth, reciprocating motion. The cleaning element may be removable.

The probe may include a cleaning assembly, such as an assembly constructed and arranged to deliver fluid toward the elongate member distal portion, such as to deliver fluid to a lens mounted to the distal portion, such as to remove mucus or other bodily fluids from the probe. The cleaning assembly may include one or more cleaning members, such as a first and a second cleaning member used to sequentially clean at least a portion of the probe. The probe may include a second cleaning assembly, where the second cleaning assembly can be similar or dissimilar to the first cleaning assembly.

The probe may include one or more positioning members to position the sensor assembly or other probe component at a predetermined distance from the tissue to be measured. The positioning members may be configured to position a portion of the probe, such as at least a portion of the sensor assembly, to a particular location or orientation relative to the multiple tissue locations. In one embodiment, the positioning members are configured to center a portion of the probe in a lumen, such as to center in a segment of the esophagus. Alternatively or additionally, the positioning members may be configured to position the portion of the probe at an off-center location, such as near a portion of a lumen wall relatively on the opposite side of the portion of the luminal wall comprising the multiple patient locations. The positioning elements may be positioned proximal and/or distal to the sensor assembly. The positioning elements may comprise one or more of a balloon and an expandable cage.

The probe may include one or more tissue tensioning members used to modify the topography of the tissue to be measured, such as to remove or reduce a fold or divot, such as a fold or divot in esophageal tissue. The tissue tensioner may be a deployable element such as a balloon, stent, or opposing arms or fingers. At least a portion of the tissue tensioner may comprise a shaped memory material such as Nitinol. Multiple tissue tensioners may be included. A sensor may be positioned in, on and/or proximate to a tissue tensioner. The tissue tensioner may be configured to radially and/or axially tension tissue.

The probe may include a luminal expander, such as to expand luminal wall tissue such as esophageal wall tissue. The luminal expander may be configured to expand tissue with a gas such as air or carbon dioxide and/or a liquid such as saline.

The probe may include a tissue temperature modifying assembly, such as an assembly to warm or cool tissue that has reached an undesired temperature, such as one or more segments of the multiple patient locations. The temperature modifying assembly may comprise substances configured to be operably activated to cause an endothermic reaction to occur, such as to cool tissue during a cardiac heat ablation procedure. Alternatively, the temperature modifying assembly may comprise substances configured to be operably activated to cause an exothermic reaction to occur, such as to warm tissue during a cardiac cryo ablation procedure. The temperature modifying assembly may be configured to spray a fluid, such as a cool fluid onto tissue. The temperature modifying assembly may comprise one or more pettier components constructed and arranged to cool at least a portion of the probe, such as tool cool tissue proximate the probe.

The probe may include a probe temperature modifying assembly constructed and arranged to modify and/or maintain the temperature of at least a portion of the probe. The probe temperature modifying assembly may be configured to cool or warm a portion of the probe, such as with circulating fluid. The probe temperature modifying assembly may comprise at least two coaxial tubes, such as two tubes surrounding one or more optical fibers and constructed and arranged to produce a thermos effect within the inner tube. The probe temperature modifying assembly may be configured to maintain the temperature of one or more electronic components, such as one or more electronic components positioned in the distal portion of the elongate member. The probe temperature modifying assembly may comprise a peltier component.

The probe may include an iso-thermal assembly constructed and arranged to cause at least a portion of the probe to tend to avoid temperature changes. The iso-thermal assembly may comprise one or more of: a thermos design; circulating fluid such as circulating fluid maintained at a relative constant temperature or circulating fluid whose temperature changes based on one or more measured temperatures of a portion of the probe; an assembly positioned proximate to at least a portion of the sensor assembly; an assembly positioned proximal to at least a portion of the sensor assembly; and an assembly positioned distal to at least a portion of the sensor assembly.

The probe may include an imaging device, such as an ultrasound imaging device or a visible light camera. Images from the imaging device may be provided on a display.

The probe may include a temperature sensor, such as a thermocouple or other temperature sensor positioned on the elongate member, such as on the distal portion of the elongate member.

The probe may include one or more markers such as radiopaque markers.

The probe may include one or more functional elements used to perform a medical procedure, such as a therapeutic or reconstructive procedure. Typical functional elements include but are not limited to: an electrode; a drug delivery element; an electromagnetic element; a heating element; a cooling element such as a peltier component; and combinations of these. One or more functional elements may be positioned on the distal portion of the elongate member, such as on or in a distal tip of the probe. The sensor may be oriented forward, along the axis of the distal portion, or may be side oriented, orthogonal to the axis of the distal portion. One or more functional elements may comprise one or more thermocouples, such as one or more thermocouples used to calibrate the probe and/or the sensor assembly.

The probe may include a signal analyzer, such as a signal analyzer that provides information based upon signals received from at least the sensor assembly. The signal analyzer may provide maximum temperature information. The signal analyzer may provide information based on a tissue location selected by an operator of the probe. The signal analyzer may include an alert assembly, such as an alert assembly configured to alarm and/or adjust an energy delivery. The alert assembly may be clinician adjustable or programmable, such as adjustable to adjust levels of temperature thresholds and/or temperature rise thresholds. The signal analyzer may compare temperature information to a library of data, such as a library including a safety map of data. The signal analyzer may compare the largest of multiple temperature readings to a threshold. The signal analyzer may create a histogram of temperature data. The signal analyzer may provide image stabilization, such as image stabilization based on signals received from a sensor of the probe, such as an accelerometer mounted in the distal portion of the elongate member. The signal analyzer may be configured to automatically zoom into or away from an area, such as an area provided on a video display. The automatic zoom may be triggered by temperature information, such as a zoom-in function triggered by one or more temperatures above a threshold in a particular portion of the multiple patient locations. A zoom-out function may be triggered when a temperature is achieved at a location outside of the currently displayed tissue portion, such as to include the location at which the above-threshold temperature occurs. The signal analyzer may be configured to provide a panning function.

The probe may include a memory storage module, such as a memory storage module configured to store time versus temperature map information. The memory module may store information selected from the group consisting of: video information; alpha-numeric information; and combinations of these.

The probe may include an error detection assembly, such as an error detection assembly configured to alarm if a temperature outside of an expected range is detected. The error detection assembly may be further configured to compensate for outlier data, wherein an alarm state is avoided if an outlier is suspected or confirmed.

The probe may include a calibration assembly, such as a calibration assembly configured to perform a calibration on the sensor assembly and/or another component or assembly of the probe. The calibration assembly may comprise a calibration algorithm or other subroutine which utilizes information received from the calibration assembly. The calibration assembly may comprise a calibration standard.

The probe may include a sterility barrier, such as a sterility barrier positioned about at least the distal portion of the elongate member.

The probe may be further constructed and arranged to produce a second map comprising non-temperature information from the multiple patient locations. The non-temperature information may comprise visual and/or ultrasound images of the multiple patient locations.

The probe may include an audible transducer. In one embodiment, the sound created by the audible transducer varies and correlates to temperature information. Sound variations may correlate to one or more of: an average of temperature readings; a maximum of temperature readings; a minimum of temperature readings; and an integration of temperature readings over time.

The probe may include a visible transducer such as a light emitting diode (LED).

The probe may include a feedback circuit, such as a feedback circuit used to control an energy delivery unit, such as a radiofrequency energy delivery unit or a cryo ablation energy delivery unit. The feedback circuit may be configured to modify energy delivery, such as to reduce or stop energy delivery. The feedback circuit may be configured to prevent energy delivery, such as to prevent energy delivery if the feedback circuit is off or otherwise detecting an undesired temperature condition. The feedback circuit may be configured to control a tissue and/or probe cooling assembly, such as to activate the cooling assembly when one or more temperature measurements are above a threshold. The feedback circuit may be configured to control a tissue and/or probe warming assembly, such as to activate a warming assembly when one or more temperature measurements are below a threshold.

The probe may comprise a lens assembly, such as a lens assembly configured to focus or otherwise direct infrared light onto one or more infrared detectors or other infrared sensors. The lens assembly may comprise one or more lenses, such as an inner lens and an outer lens.

The probe may comprise a noise reduction algorithm, such as to reduce infrared noise or other thermal noises. The noise reduction algorithm may be configured to reduce or otherwise filter one or more predetermined sources of noise, such as one or more predetermined sources of infrared radiation.

The probe may include one or more tools, such as one or more tools selected from the group consisting of: energy delivery elements such as radiofrequency electrodes; lasers; ultrasonic crystals; saws; drills; electrocautery devices; coagulators; laparoscopic tools; and combinations of these.

According to another aspect, a system including a temperature monitoring probe in accordance with the present inventive concepts and a laparascopic tool is provided. The probe sensor assembly may be positioned on and/or in, or otherwise integrated into the laparoscopic tool. The probe elongate member may comprise the shaft of the laparoscopic tool.

According to another aspect, a system including a temperature monitoring probe in accordance with the present inventive concepts and a bone cutter is provided. The bone cutter may comprise a drill and/or a saw. The probe's multiple patient locations may comprise tissue being cut and/or tissue proximate the tissue being cut.

According to another aspect, a system including a temperature monitoring probe in accordance with the present inventive concepts and an energy delivery assembly is provided. The energy delivery assembly may be configured to deliver energy selected from the group consisting of: laser energy; radiofrequency energy; cryogenic fluid energy; microwave energy; mechanical energy; chemical energy; electromagnetic energy; and combinations of these. The energy delivery assembly may be positioned in the probe's elongate member distal portion, such as at, on or near the probe's distal end. The probe's multiple patient locations may comprise tissue to which energy is being delivered and/or tissue proximate the tissue receiving the energy.

According to another aspect, a system including a temperature monitoring probe in accordance with the present inventive concepts and a magnetic resonance imaging (MRI) device is provided. The probe is constructed and arranged to detect heat produced during an MRI imaging procedure, such as heat occurring at or proximate to one or more ferromagnetic material in, on or near the patient being imaged.

According to yet another aspect, a method of producing a temperature map comprising temperature information for multiple patient locations is disclosed. A probe is provided including a sensor assembly and an elongate member. The elongate member includes a proximal portion and a distal portion.

BRIEF DESCRIPTION OF THE DRAWINGS

The accompanying drawings, which are incorporated in and constitute a part of this specification, illustrate various embodiments of the present inventive concepts, and together with the description, serve to explain the principles of the inventive concepts. In the drawings:

FIGS. 3A and 3B illustrate side and end sectional views, respectively, of the distal portion of an ablation and forward viewing temperature measurement probe, consistent with the present inventive concepts;

FIG. 4A illustrates a side sectional view of an elongate member of a side viewing temperature probe with a translating sensor, consistent with the present inventive concepts;

FIG. 4B illustrates a side sectional view of the temperature probe of FIG. 4A, with the sensor advanced, consistent with the present inventive concepts;

FIG. 15A illustrates a side view of the distal portion of a side viewing temperature measurement probe with a cleaning wiper, consistent with the present inventive concepts;

FIG. 15B illustrates the temperature measurement probe of FIG. 15A with the cleaning wiper advanced, consistent with the present inventive concepts;

DETAILED DESCRIPTION OF THE DRAWINGS

Reference will now be made in detail to the present embodiments of the inventive concepts, examples of which are illustrated in the accompanying drawings. Wherever possible, the same reference numbers will be used throughout the drawings to refer to the same or like parts.

Provided herein is a temperature measurement probe for producing a temperature map for multiple locations, such as a surface of tissue for a patient. The probe may include one or more sensors, such as infrared light detectors or other infrared sensors. The probe may include a reusable portion, and one or more disposable portions. The probe may include an elongate member, and measure temperature at multiple locations positioned at the side of the elongate member and/or forward of the distal end of the elongate member.

Figure 1:
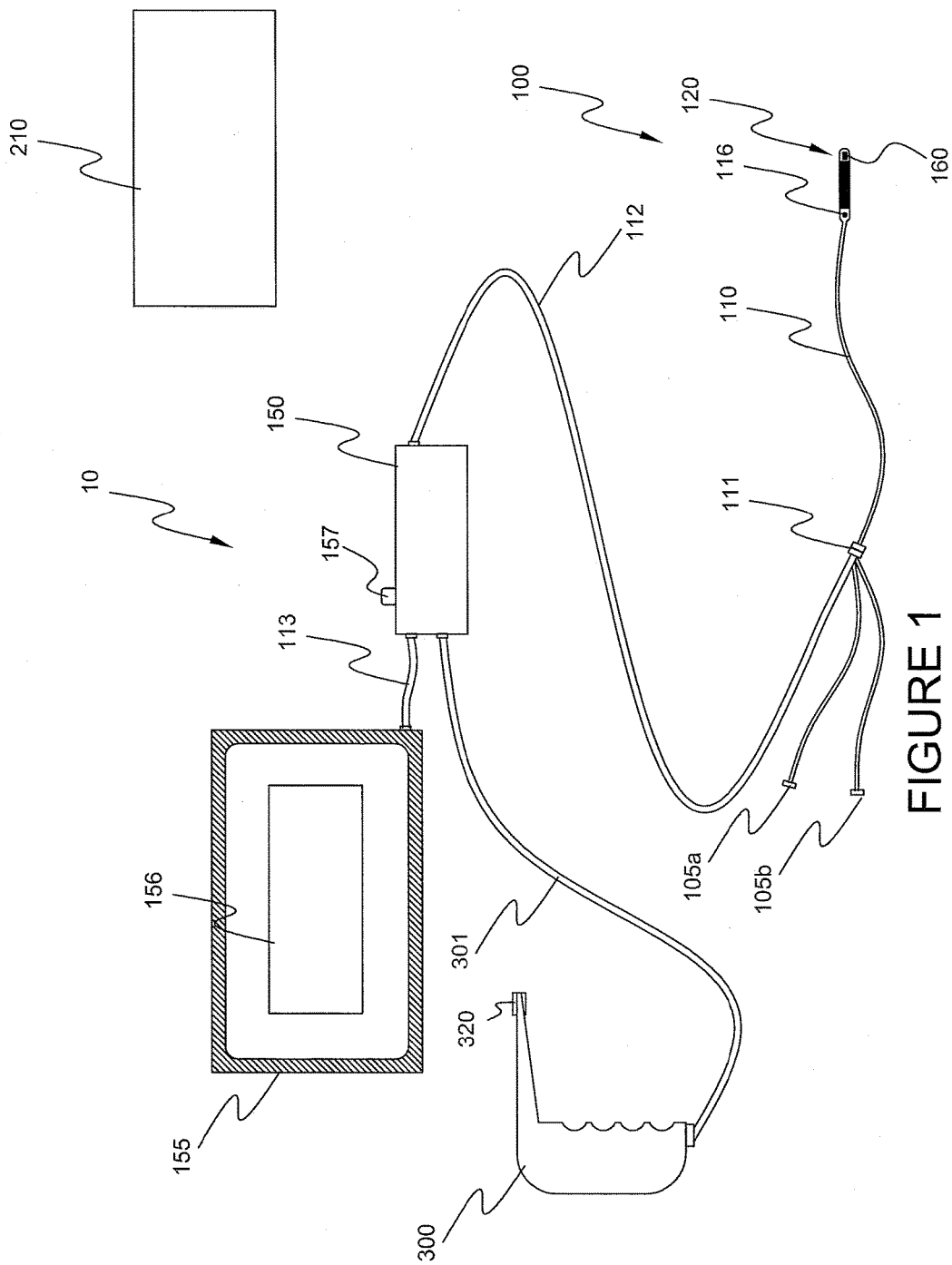
FIG. 1 illustrates a schematic view of a system including a temperature measurement probe, consistent with the present inventive concepts.

Referring now to FIG. 1, a system of the present inventive concepts is illustrated. System 10 includes luminal temperature measurement device 100, electronic module 150, and display 155. Device 100 may be configured to be placed into a patient, such as into a lumen within the body of a patient. System 10 is configured to produce a temperature map of multiple patient locations. Typical patient locations include but are not limited to: one or more continuous tissue areas, multiple discrete locations, one or more locations on a single plane or two or more locations on multiple planes. Device 100 includes shaft 110 which includes connector 111 at its proximal end. Shaft 110 may be rigid, flexible, or include both rigid and flexible portions. Device 100 is attached to electronic module 150 via cable 112. Cable 112 may be configured to perform one or more functions, including but not limited to: providing power or transmitting a force; sending or receiving electrical signals such as via wires; sending or receiving optical signals such as via fiber optic cables; transmitting acoustical signals such as sound waves; and transmitting solids, liquids or gases such as via one or more lumens.

A first portion of sensor assembly 120 is positioned at the distal end of shaft 110 and is configured to provide temperature information for multiple patient locations, such as multiple tissue locations. In one embodiment, sensor assembly 120 is configured to gather, measure and/or process infrared signals to determine temperature information, such as when device 100 comprises a passive or active infrared detector or detector array. Sensor assembly 120 may comprise a lens assembly such that infrared or other energy can be directed toward a sensor at a second portion of the sensor assembly located at another location in device 100 and/or electronic module 150. Typical sensors used to measure the temperature information include but are not limited to: infrared sensors such as active or passive infrared sensors or sensor arrays; thermocouple or thermocouple arrays, thermopiles such as a bolometer; thermisters; thermochromic elements; pyrometers; liquid crystal temperature detectors such as thermotropic liquid crystals; fluorescent sensors; and sensors including leuco dyes and combinations of these.

Alternatively or additionally, device 100 and sensor assembly 120 are configured to detect a non-temperature tissue change, such that system 10 can process this tissue change information to produce a temperature map for multiple patient locations. These tissue changes include but are not limited to: tissue color changes; cellular structure changes such as cellular expansion; tissue conductivity changes; tissue density changes; and combinations of these. These non-temperature signals may correlate to an absolute temperature of tissue or a change in temperature of tissue.

Alternatively or additionally, device 100 and sensor assembly 120 are configured to detect a substance produced by tissue, such that system 10 can process this substance production information to produce a temperature map for multiple patient locations. Substance production information may include but are not limited to: one or more substances associated with cellular damage; gas production; smoke production; and combinations of these.

Sensor assembly 120 may include various optical components to focus, transmit, split, reduce, filter, communicate or otherwise handle light such as infrared light. Typical components include but are not limited to: lenses; mirrors; filters; fiber optic cable; prisms; amplifiers; refractors; splitters; polarizer; and other optical components well known to those of skill in the art. In one embodiment, optical components focus infrared light on a sensor or sensor array integral to sensor assembly 120. The one or more optical components may be fixedly mounted in device 100 or may be moved such as with rotational, translational, reciprocal, orbital and/or other movement assemblies such as MEMS assemblies.

Sensor assembly 120 provides temperature information to electronic module 150. This information may be transmitted by one or more conductors such as wires or fiber optic cables, or may be transmitted wirelessly. In a particular embodiment, the first portion of sensor assembly 120 provides temperature information in the form of infrared light which is transmitted through shaft 110 (e.g. deflected with a series of mirrors) to an infrared sensor array at the second portion of the sensor assembly in a proximal portion of device 100 and/or within electronic module 150. In another embodiment, sensor assembly 120 is connected to a fiber optic cable, such as a cable that is of low impedance or transparent (zero impedance) to infrared light or a band of infrared light, and connected to a lens or other optical component assembly which directs the infrared light to an infrared sensor array in a proximal portion of device 100 and/or within electronic module 150. In yet another embodiment, sensor assembly 120 includes an infrared sensor array, and one or more electrical conductors such as wires travel proximally in shaft 110 and communicate temperature information to electronic module 150.

Device 100 may include a visible light camera constructed and arranged to provide a visible picture of one or more patient locations, such as one or more locations in the patient's esophagus. In a particular embodiment, a visible light picture is provided on display 155 of the same or similar multiple patient locations that are recorded by sensor assembly 120.

Proximate sensor assembly 120 is port 116, such as a port configured to deliver fluid to sensor assembly 120 or tissue proximate sensor assembly 120. Shaft 110 may include one or more lumens, not shown but fluidly or otherwise operably connected to cable 112, port 105a or port 105b, such as to provide inflation fluid such as to inflate a balloon, to deliver one or more agents such as a cooling or warming fluid or a drug to port 116, or to slidingly receive a fiber or fiber bundle such as a cable linkage, an optical fiber or fiber bundle, or a conductor or conductor bundle.

Device 100 may include one or more functional elements, such as functional element 160 located proximate sensor assembly 120. Functional element 160 is typically a sensor or a transducer, such as an element selected from the group consisting of: an electrode; a drug delivery element; an electromagnetic transducer; a heating or cooling element; and combinations of these. Functional element 160 may be a sensor, such as a thermocouple or other temperature sensor. In a particular embodiment, functional element 160 is a temperature sensor configured to be used in a calibration of sensor assembly 120.

Located at the proximal end of shaft 110 are ports 105a and 105b. Ports 105a and 105b are operably connected to one or more lumens of shaft 110, not shown but preferably providing a connection to one or more locations along shaft 110, such as port 116, functional element 160 and/or sensor assembly 120. Ports 105a and/or 105b may be attachable to a fluid delivery device, such as an infusion pump or a syringe, such that fluid such as saline can be used to clean a portion of device 100, heat or warm tissue proximate sensor assembly 120, and/or provide another function.

Device 100 may include one or more stabilization portions, not typically located near the proximal end of shaft 110 or along cable 112 and configured to position and/or prevent undesired motion of device 100. Typical stabilization portions may include a clip, a mouth piece such as a mouth piece used to position shaft 110 in the esophagus of the patient, a vacuum assembly, and combinations of these.

Electronic module 150 receives signals from sensor assembly 120 of device 100. These signals represent a temperature map of multiple patient locations in proximity to sensor assembly 120. Sensor assembly 120 may produce electrical signals such as signals received from electronics integral to sensor assembly 120, not shown but preferably electronics common to visible light and infrared camera products. Alternatively or additionally, the signals may be optical signals such as infrared signals received from sensor assembly 120 and transmitted via optical fibers included in shaft 110 and cable 112. In one embodiment, connector 111 may include an electronic assembly which converts optical signals to electrical signals, such as when connector 111 receives optical signals from a fiber bundle contained within shaft 110, and transmits electrical signals to electronic module 150 through wires in cable 112.

Electronic module 150 processes the signals received from sensor assembly 120 to produce information representing a temperature map of the multiple patient locations viewed by sensor assembly 120. The temperature information may be presented on display 155 such as via signals transmitted through cable 113 such that temperature map 156 is shown on display 155. Alternatively or additionally, temperature information may be transmitted to display 155 via a wireless transceiver. Temperature map 156 may be presented in a number of forms including but not limited to a tabular display of alphanumeric values representing the temperature of the multiple patient locations, or a graphical picture such as a color picture in which temperatures are represented by color shades or hues.

Electronic module 150 may include alarm transducer 157, such as a transducer selected from the group consisting of: an audible transducer, a visible transducer such as a light emitting diode (LED), a tactile transducer, or other element configured to alert an operator of a condition such as an alarm, alert, warning, or other condition (hereinafter "alarm") in which an operator of the system is to be notified. Module 150 may process the information received from sensor assembly 120 to determine when a condition exists in which alarm transducer is to be activated. Alarm conditions may be adjustable, such as via a user interface, not shown, but integral to electronic module 150 or another component of system 10. In one embodiment, the condition is determined by comparison to a threshold, such as a threshold adjustable by an operator of system 10. Alarm conditions may be based on the current temperature map and/or a cumulative or other mathematically processed representation of values of the temperature map such as cumulative historic values of multiple patient locations. In a particular embodiment, system 10 provides current and historic temperature information for multiple patient locations, the information including but not limited to: current temperature; average temperature; maximum temperature; minimum temperature; slope of temperature change; and integration of temperature over time. The various types and forms of recorded and calculated temperature information can be presented to the operator via display 155, another display or memory component. Alternatively or additionally, the various types and forms of recorded and calculated temperature information can be compared to one or more alarm thresholds such as to activate alarm transducer 157. In a particular embodiment, when an alarm condition is entered, system 10 or a separate system may be controlled by system 10, such as to cease power delivery when a maximum temperature is achieved.

Electronic module 150 may include a memory storage module, such as a module configured to store temperature and/or other types of information including but not limited to: historic information such as temperature versus time information, pre-determined threshold information such as information related to maximum temperatures allowable for a particular tissue or tissue type, calculated information such as an integration of time at temperature for a tissue location; calibration information such as historic calibration information and data used to perform a calibration procedure; alarm information such as historic alarm conditions or data used to determine when system 100 has entered an alarm state; and other information.

Electronic module 150 may include a signal analyzer, such as a signal analyzer which may be used or modified by the operator. Inputs and outputs of the signal analyzer may be shown on display 155, such as in displaying temperature information for a particular tissue location. The signal analyzer may allow zooming, such as to zoom into a particular site of tissue, and the site location may be manipulated by the operator, such as through a user interface (not shown).

System 10 may include visualization instrument 210, such as a visualization instrument selected from the group consisting of: an MRI, a Ct scanner, a fluoroscope or other x-ray instrument; and combinations of these. In one embodiment, visualization instrument 210 is an MRI, and system 10 is used to detect heat, such as undesired heat, caused by the interaction between an MRI and one or more pieces of metal implanted in a patient.

Alternative or in addition to device 100, system 10 includes tool 300 which is connected to electronic module 150 via cable 301. Tool 300 includes sensor assembly 320, a forward looking infrared sensor assembly configured to visualize multiple patient locations, such as a surface of bone or other tissue being treated by tool 300. Tool 300 may be a tool selected from the group consisting of: a laparoscopic tool such as a laparoscopic radiofrequency (RF) energy ablation tool; a bone cutting tool such as a bone cutting saw; a drill; and combinations of these. In a typical application, the multiple patient locations is bone being drilled or cut into, and system 10 is configured to prevent overheating of patient tissue.

System 10 typically includes both disposable and reusable components. In one embodiment, device 100 including shaft 110, sensor assembly 120, and cable 112 are disposable (e.g. used for a single patient procedure only), while electronic module 150 and display 155 are reusable. In another embodiment, cable 112 is reusable. In another embodiment, a disposable sheath surrounds a reusable device 100 including reusable shaft 110 and reusable sensor assembly 120.

Figure 2A:
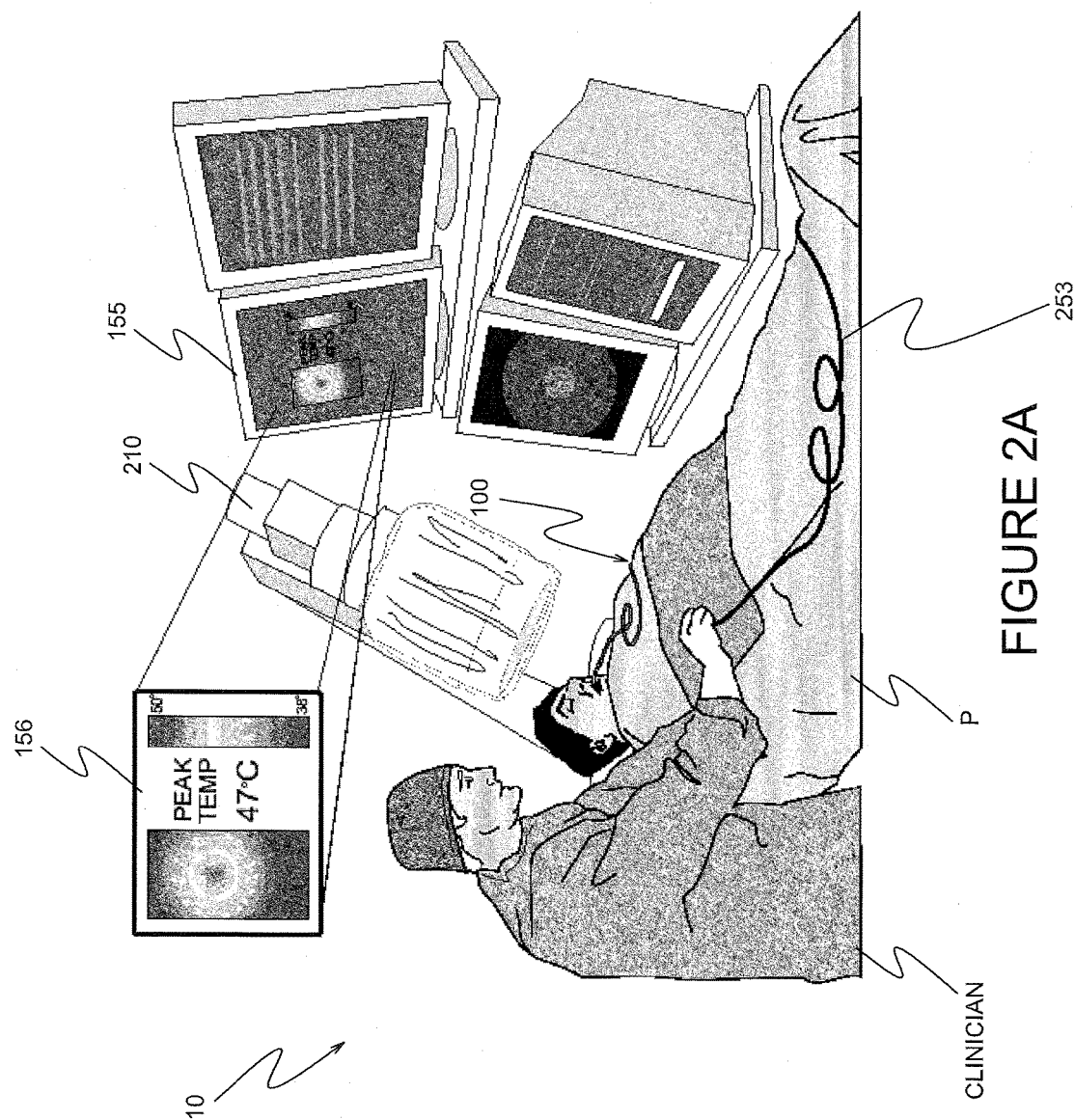
FIG. 2A illustrates a side view of a clinical procedure including an ablation catheter and an esophageal temperature probe, consistent with the present inventive concepts.

Referring now to FIG. 2A, a method of the present inventive concepts is illustrated in which a patient is receiving an ablation procedure, such as a cardiac ablation procedure to treat atrial fibrillation (AF). Ablation catheter 253 is inserted into the vasculature of the patient and advanced to patient P's heart. An energy delivery unit, not shown, connects to catheter 253 such that catheter 253 delivers ablation energy to patient P's heart. Ablation is typically achieved by heating or cooling tissue (e.g. left atrial or right atrial tissue) through the use of radiofrequency (RF) energy; laser energy; cryogenic energy; subsonic energy; acoustic energy; ultrasound energy; microwave energy; chemical energy; and combinations of these.

System 10 includes device 100 which has been inserted into the esophagus of patient P by a clinician. System 10 includes display 155 which provides temperature map 156 of multiple locations within patient P's esophagus. Temperature map 156 and other information provided on display 155 or another display device (not shown), may utilize various alphanumeric or other graphical properties to differentiate temperature or other information. In a preferred embodiment, different temperatures are differentiated through the change in one or more of: color; shade; contrast; hue; saturation; and brightness. Alternatively or additionally, alphanumeric information may be differentiated by varying one or more of: boldness; font type and size. Information such as temperature information may be correlated to one or more characteristics such as color. In a particular embodiment, the correlation algorithm is adjusted by a clinician. For example, the clinician may set a particular shade of red to a particular temperature level. Alternatively or additionally, sound may be used to represent temperature information, such as sound that changes in pitch or volume as temperature changes, and the correlation between temperature level and a sound parameter may be adjustable by a clinician.

In addition to temperature map 156, system 10 may provide numerous forms of information provided by the sensor assembly of device 100 or one or more other sensors or functional elements of device 100. Such information may be information that is processed by one or more algorithms of system 10, such as by electronic module 150 of FIG. 1. Typical temperature information includes but is not limited to: average temperature; cumulative temperature; maximum and minimum temperatures; range of temperatures over time; and rate of change of temperature. Other information provided includes but is not limited to: time of day; date; patient ID; clinician ID; location of procedure; multiple patient location anatomical description; EKG information; energy delivered information; and other patient physiologic information. Information provided can be in alphanumeric and/or graphical forms.

Also depicted in FIG. 2A is visualization instrument 210. Visualization instrument 210, typically a real time x-ray unit or fluoroscope, provides internal images of the patient's anatomy.

Figure 2B:
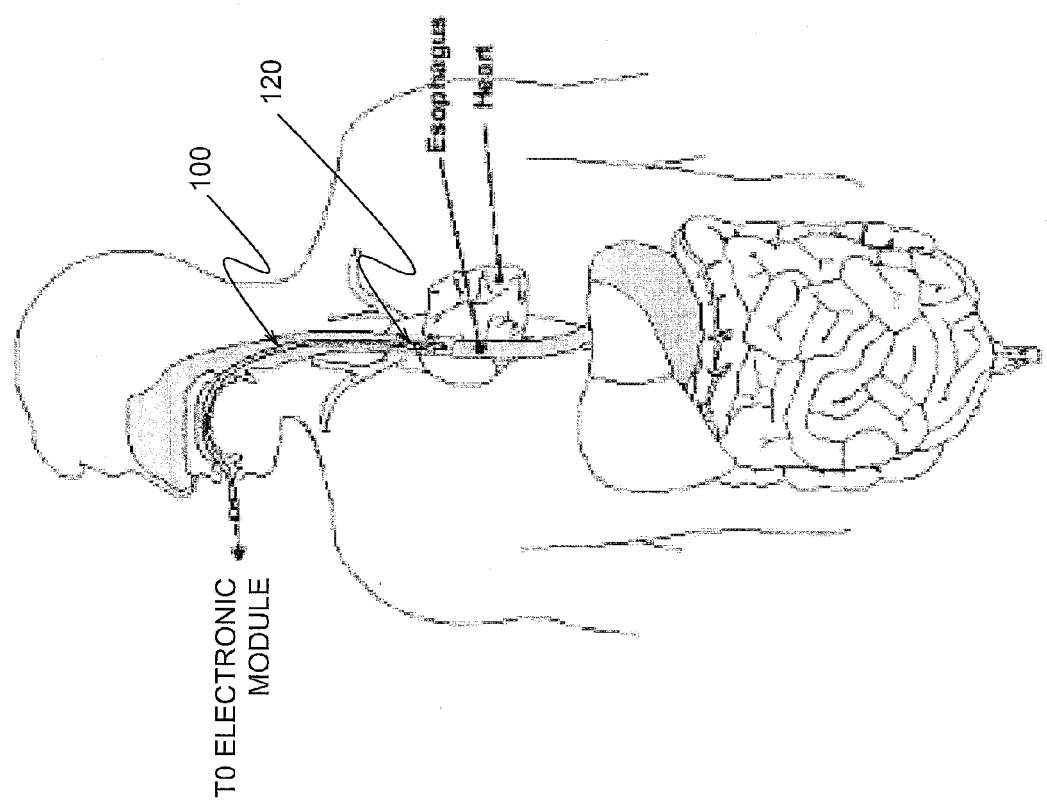
FIG. 2B illustrates a side sectional view of the esophageal temperature probe of FIG. 2A, consistent with the present inventive concepts.

Referring now to FIG. 2B, a cross-sectional image of patient P of FIG. 2A is shown. Device 100 has been inserted into the esophagus such that sensor assembly 120 is positioned proximate the patient's Heart. During an ablation procedure, sensor assembly 120 and device 100 are used to provide temperature map information configured to prevent damage to the Esophagus while the patient's Heart is heated and/or cooled. Of particular interest to the clinician is delivery of energy to the posterior wall of the patient's Heart, due to the proximity and potential contact between the Heart and the Esophagus.

Figure 2C:
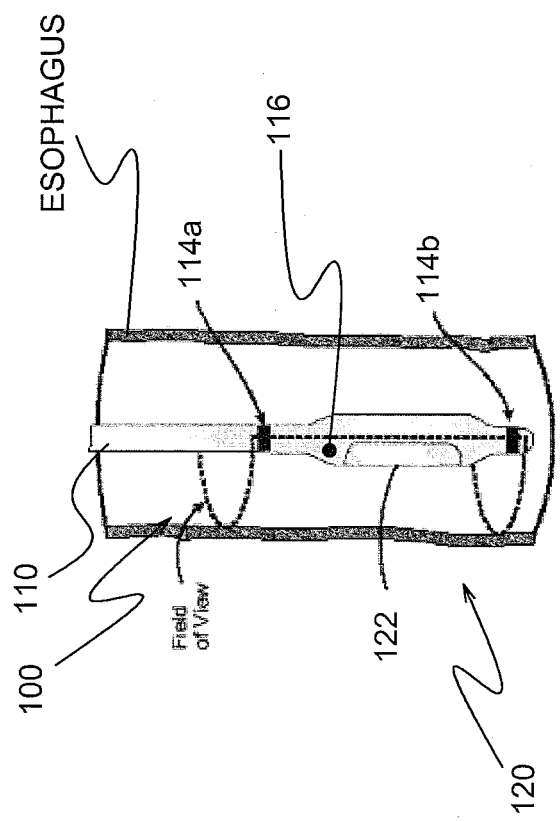
FIG. 2C illustrates a magnified side sectional view of the temperature probe of FIG. 2B, consistent with the present inventive concepts.

Referring now to FIG. 2C, a cross sectional image of the patient P's Esophagus of FIGS. 2A and 2B is illustrated. Device 100 has been advanced to the location shown in FIG. 2B, and rotated to the position shown in FIG. 2C. Sensor assembly 120 includes lens 122, typically 0.5" to 4" in length, which is positioned at tissue locations of the Esophagus that are most proximate the patient's heart. Sensor assembly 120 is configured to measure temperature at locations relatively orthogonal to shaft 110 and without contacting the wall of the Esophagus. Shaft 110 includes marker 114a and marker 114b, proximal and distal, respectively, to sensor assembly 120. Markers 114a and 114b are typically radiopaque markers that are visible to visualization instrument 210 of FIG. 2a. Alternatively or additionally, markers 114a and 114b may be markers selected from the group consisting of: ultrasonically reflective markers; electromagnetic markers; visible markers; and combinations of these.

Shaft 110 further includes port 116, configured to deliver one or more fluids from shaft 110. Fluids may be delivered from port 116 to cool or warm tissue being monitored by sensor assembly 120, such as fluids delivered manually or automatically by system 10 when one or more patient locations exceed one or more temperature thresholds. Alternatively or additionally, fluids such as saline may be delivered from port 116 to remove debris covering lens 122.

Referring now to FIGS. 3A and 3B, a temperature measurement probe of the present inventive concepts is illustrated in which the probe delivers energy and produces a temperature map of multiple patient locations in front of its distal end. A distal portion of shaft 110 includes sensor assembly 120 comprising lens 122 and an array of sensors 121. Sensors 121 are typically an infrared CCD array or other array configured to record infrared light information corresponding to a temperature range, such as a temperature range between 30° C. and 70° C. Sensors 121 are connected to wire bundle 128 which travel proximally and carry information and/or power to or from sensors 121 as has been described in detail hereabove.

The distal end of shaft 110 further includes an electrode, functional element 160, which is typically configured to deliver energy such as RF energy. Alternatively or additionally, functional element 160 may deliver energy selected from the group consisting of: laser energy; cryogenic energy such as energy delivered by flowing cryogenic fluid such as liquid nitrogen proximate the tissue to be ablated; microwave energy; mechanical energy; chemical energy; electromagnetic energy; and combinations of these.

Lens 122 and sensors 121 are constructed and arranged to provide a temperature map for the tissue proximate functional element 160 prior to, during, and after delivery of energy by functional element 160.

Referring now to FIG. 4A, a sectional side view of a side-viewing temperature measurement probe of the present inventive concepts is illustrated in which a sensor is advanced and/or retracted to create a temperature map of multiple patient locations. Device 100 includes at its distal end, lens 122. Positioned within lens 122, is sensor 121, typically a sensor configured to measure and/or transmit infrared light received through lens 122. Sensor 121 may be configured to measure and/or transmit infrared light for a single patient location (i.e. a point) or multiple locations. In an alternative embodiment, sensor 121 and/or another component of device 100 may be configured to record visible light information or other information such as ultrasound information.

In one embodiment, sensor 121 includes multiple sensors configured to measure temperature at multiple patient locations such as locations extending radially out from sensor 121 and covering a circumference of 10° or more, typically 90° or greater, and more typically greater than 180°. In a particular embodiment, sensor 121 records temperature information at patient locations located at a full circumference (i.e.) 360° at a range of locations at sensor 121 that are perpendicular to shaft 110. Alternatively or additionally, drive assembly 170 may rotate shaft 123 and sensor 121, such as a full 360° rotation or a partial rotation less than 360°, typically 180° or less or 90° or less, as is described in reference to FIG. 5 herebelow. Alternatively or additionally, lens 122 may be constructed and arranged to move and/or reshape, such as with one or more MEMS mechanisms.

Sensor 121 is attached to drive shaft 123 and is shown in a retracted position. Device 100 includes linear drive assembly 170 which includes drive gear 171 and lead screw 172. Drive assembly 170 is configured to advance and/or retract shaft 123 and sensor 121 at one or more velocities.

Referring now to FIG. 4B, shaft 123 and sensor 121 have been advanced to the distal portion of lens 122. During advancement and retraction of sensor 121, temperature information is recorded at multiple tissue locations proximate to and along the length of lens 122. Temperature map information created by the system of FIGS. 4A and 4B can be provided in numerous forms, preferably a two-dimensional display of three dimensional tissue surrounding lens 122. While the temperature information is recorded sequentially, a full temperature map may be displayed simultaneously in which particular patient location temperature information is updated as it is recorded and processed, techniques well known to those of skill in the art in creating visible images and ultrasound images from translating and/or spinning cameras, CCD arrays, ultrasound crystals and other sensors.

Figure 5:
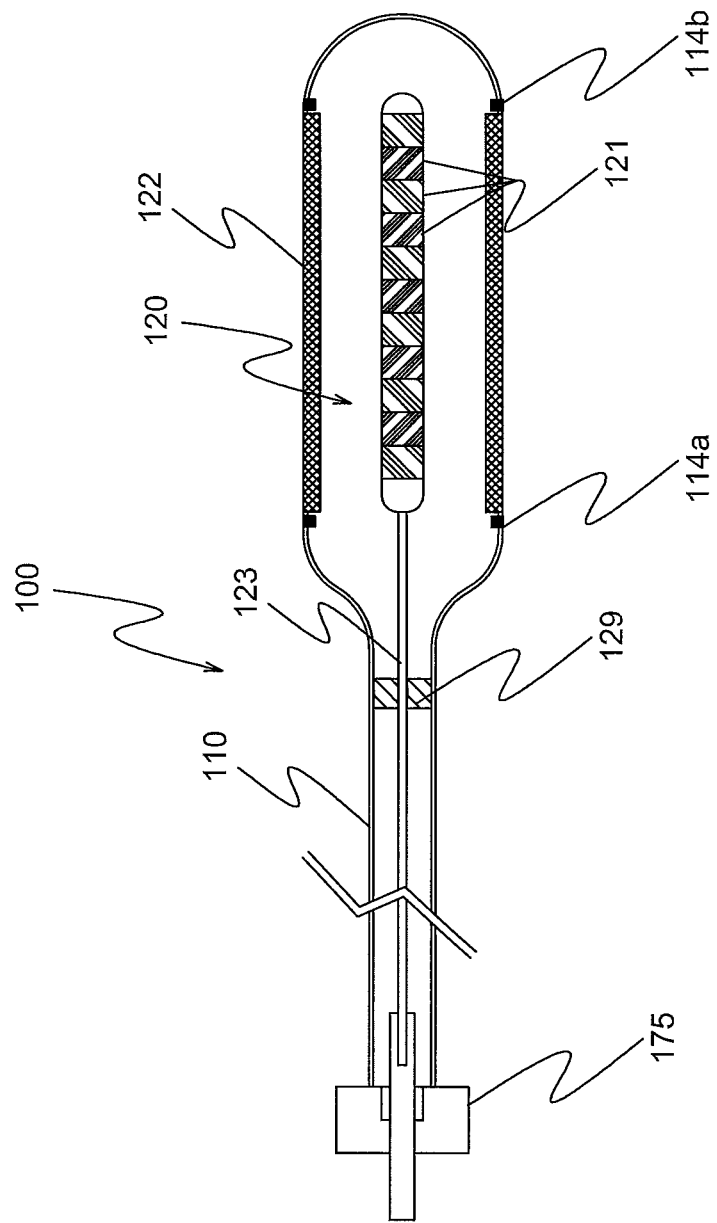
FIG. 5 illustrates a side sectional view of the distal portion of a side viewing temperature probe with a rotating array of sensors, consistent with the present inventive concepts.

Referring now to FIG. 5, a sectional side view of a side-viewing temperature probe of the present inventive concepts is illustrated comprising a spinning sensor assembly. Device 100 comprises lens 122 positioned on the end of shaft 110. Lens 122 is configured to focus infrared light received from tissue surrounding lens 122 onto sensor assembly 120. Surrounding lens 122 are circumferential markers 114a and 114b, proximal and distal to lens 122, typically radiopaque markers used to identify the position of sensor assembly 120 under fluoroscopy. Sensor assembly 120 is typically a linear array of similar or dissimilar infrared light sensors 121. In an alternative embodiment, lens 122 comprises an inner and outer lens.

Sensor assembly 120 is mechanically attached to and rotated by drive shaft 123 which is centrally positioned within the lumen of shaft 110 by guide bushing 129. Drive shaft 123 is rotated by rotational drive assembly 175. Shaft 123 is typically rotated a full 360°, however partial rotations of 180° or less, or 90° or less may be performed. While being spun, sensor assembly 120 records a temperature map of the tissue surrounding sensor assembly 120, such as the wall tissue of a lumen of a patient, such as esophageal wall tissue.

Figure 6:
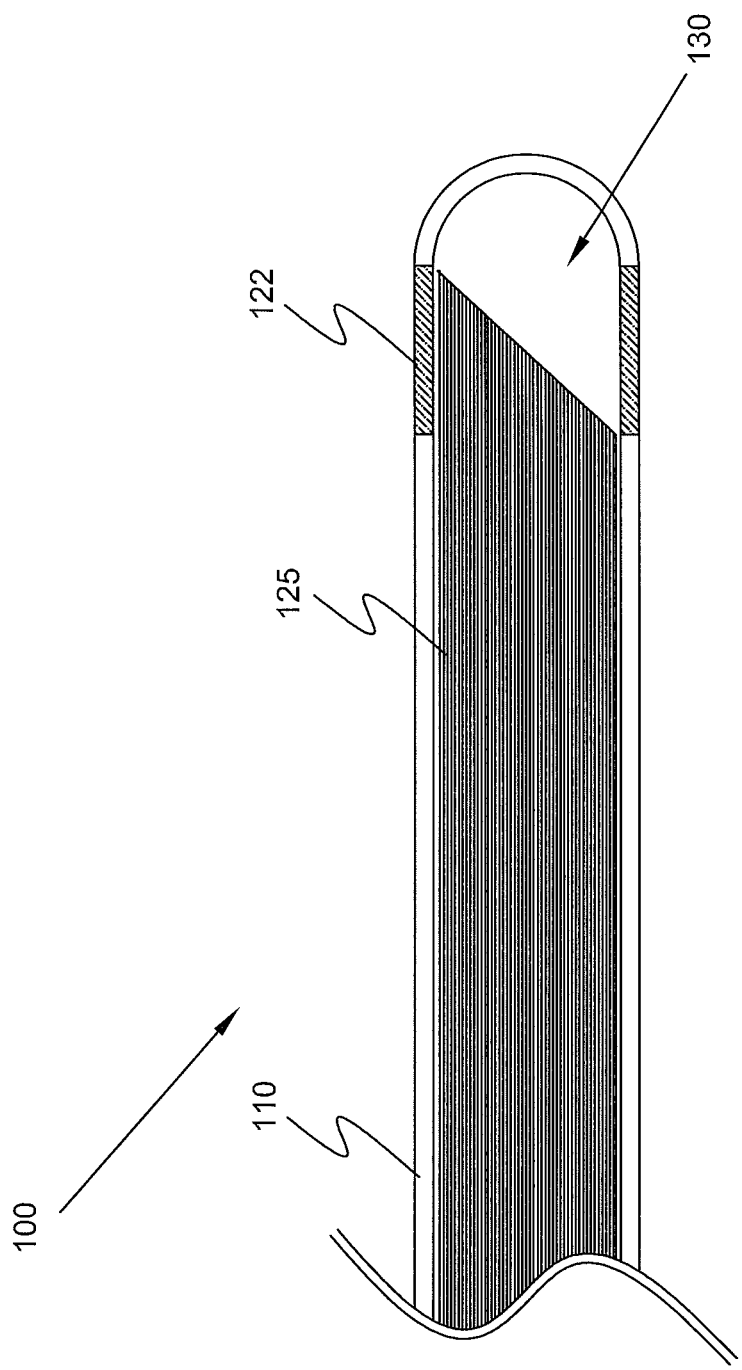
FIG. 6 illustrates a side sectional view of the distal portion of a side viewing temperature probe with a fiber bundle with beveled end, consistent with the present inventive concepts.

Referring now to FIG. 6, a sectional side view of a side-viewing temperature probe of the present inventive concepts is illustrated comprising a solid cylinder surrounding an array of optical fibers that have been assembled in a coherent fiber optic bundle. Device 100 includes shaft 110, a solid cylinder shaft that may be flexible or rigid. Shaft 110 surrounds fiber optic bundle 130 comprising a coherent bundle of optical fibers 125, such as optical fibers which have little or no impedance to infrared radiation. Bundles may be arranged with as few as one, to as many as tens of thousands of individual fibers. Fibers may be coated or uncoated, clad or unclad, and can range in diameter from 50 to 700 microns. The shape of the bundles can be circular of rectangular. In a particular configuration, a rectangular 60×60 fiber bundle includes 3600 individual fibers, each producing temperature information for a discrete tissue location. In an alternative embodiment, a single fiber 125 is contained within shaft 110. In one embodiment, the fiber or fibers are comprised of germanium and/or silver halide, however numerous types of fibers may be used such as fibers constructed of materials selected from the group consisting of: germanium; arsenic; selenium; sulfur; tellurium; silver halide; and combinations of these. Amorphous Materials Inc. of Garland, Tex. is a manufacturer of applicable optical fibers such as their products AMTIR-1, AMTIR-2, AMTIR-3, AMTIR-4, AMTIR-5, AMTIR-6, and C1.

The distal end of fiber optic bundle 130 is arranged at an angle such that infrared or other radiation passing through lens 122 is received by the beveled end of each fiber 125. The bevel angle may be chosen to maximize absorption of the received radiation. In a particular embodiment, a 45° bevel angle is used. Fiber bundle 130 may be rotated, such as a full 360° rotation, by one or more rotating drive assemblies (e.g. drive assemblies used in medical imaging products device industry to rotate fibers or fiber bundles), not shown. Alternatively, partial rotations of 180° or less, or 90° or less may be performed such as to create a less than full circumferential view of a lumen such as the esophagus of a patient.

In communication with fiber bundle 130 is a sensor assembly, not shown but typically proximal to shaft 110 or included in a proximal portion of shaft 110. The sensor assembly, typically an infrared sensor assembly comprising an array of infrared sensors, receives the radiation signals passed through lens 122 into fiber optic bundle 130. Lens 122 is shown as a circumferential ring that directs, focuses or otherwise lets radiation pass through lens 122 onto the beveled end of fiber optic bundle 130.

Figure 7:
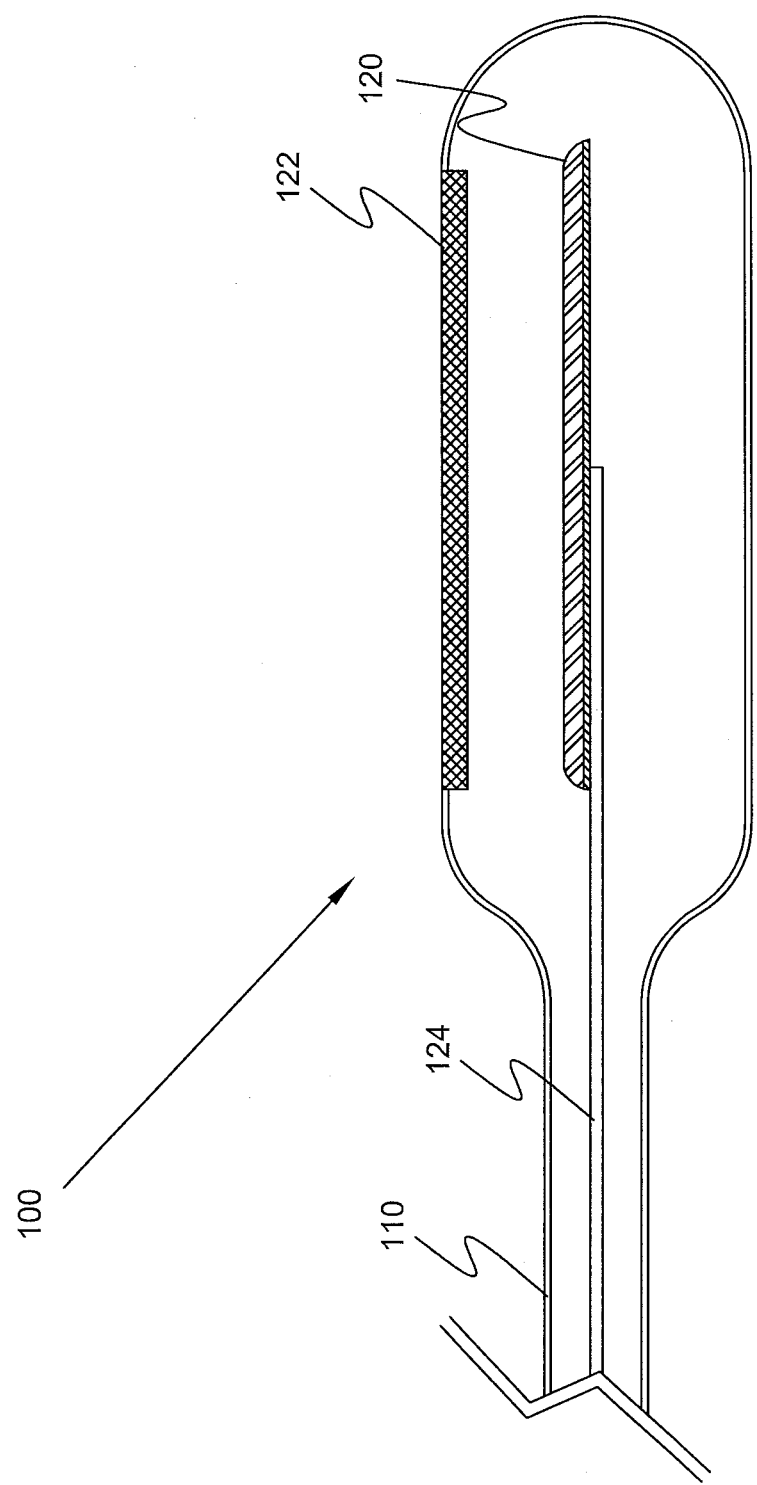
FIG. 7 illustrates a side sectional view of the distal portion of a side viewing temperature probe with a sensor array attached to a shaft, consistent with the present inventive concepts.

Referring now to FIG. 7, a sectional view of a side-viewing temperature probe of the present inventive concepts is illustrated comprising an enlarged distal portion including a sensor assembly and a partial circumferential lens. Device 100 includes shaft 110 which surrounds sensor assembly 120 and drive shaft 124. A partial circumferential lens 122 is positioned relative to sensor assembly 120. In an alternative embodiment, lens 122 is a full circumferential (e.g. 360°) lens, such as when sensor assembly 120 is a full 360° viewing sensor. Lens 122 is constructed and arranged to direct, focus or otherwise allow radiation to pass onto sensor assembly 120. Lens 122 may be selected from the same group of materials as infrared transparent fibers discussed hereabove.

Sensor assembly 120 includes an array of infrared sensors, typically an infrared CCD array or other array configured to record infrared light information. Infrared arrays may be configured to produce temperature maps based on an array of pixels, such as an array with a minimum of 10 pixels by 10 pixels. Arrays of 100 by 100 or more pixels may be used, such as to represent an area of esophageal tissue with a length of one inch or more at an area proximate a patient's heart. Sensor assembly 120 may include integrated circuitry, such as to perform one or more of the following functions: process signals received by sensor assembly 120; multiplex signals; filter signals; combine signals; amplify signals; and convert electrical signals to optical signals for fiber optic transmission.

Sensor assembly 120 mechanically connects to shaft 124 such as to position sensor assembly relative to lens 122. Lens 122 may be used to magnify or demagnify a viewed location, and may be used to expand the field of view. Lens 122 may be configured to be focused, manually or automatically, in a similar configuration used in visible light cameras. Additionally, shaft 124 may be configured to act as an information transmission conduit to the proximal portion of device 100. For example, shaft 124 may be used to send and/or receive information and/or power to or from sensor assembly 120. Typically, shaft 124 includes a bundle of wires that communicate with sensor assembly 120. However, in an alternative embodiment, shaft 124 may include optical fibers and sensor assembly 120 includes electronics configured to convert sensor information into optical data.

In yet another embodiment, shaft 124 may rotate a full 360° rotation, by one or more rotating drive assemblies, not shown. Alternatively, partial rotations of 180° or less, or 90° or less may be performed. Here, lens 122 would typically be 360° or a sufficient circumferential sector to accommodate the motion of sensor assembly 120.

Figure 8:
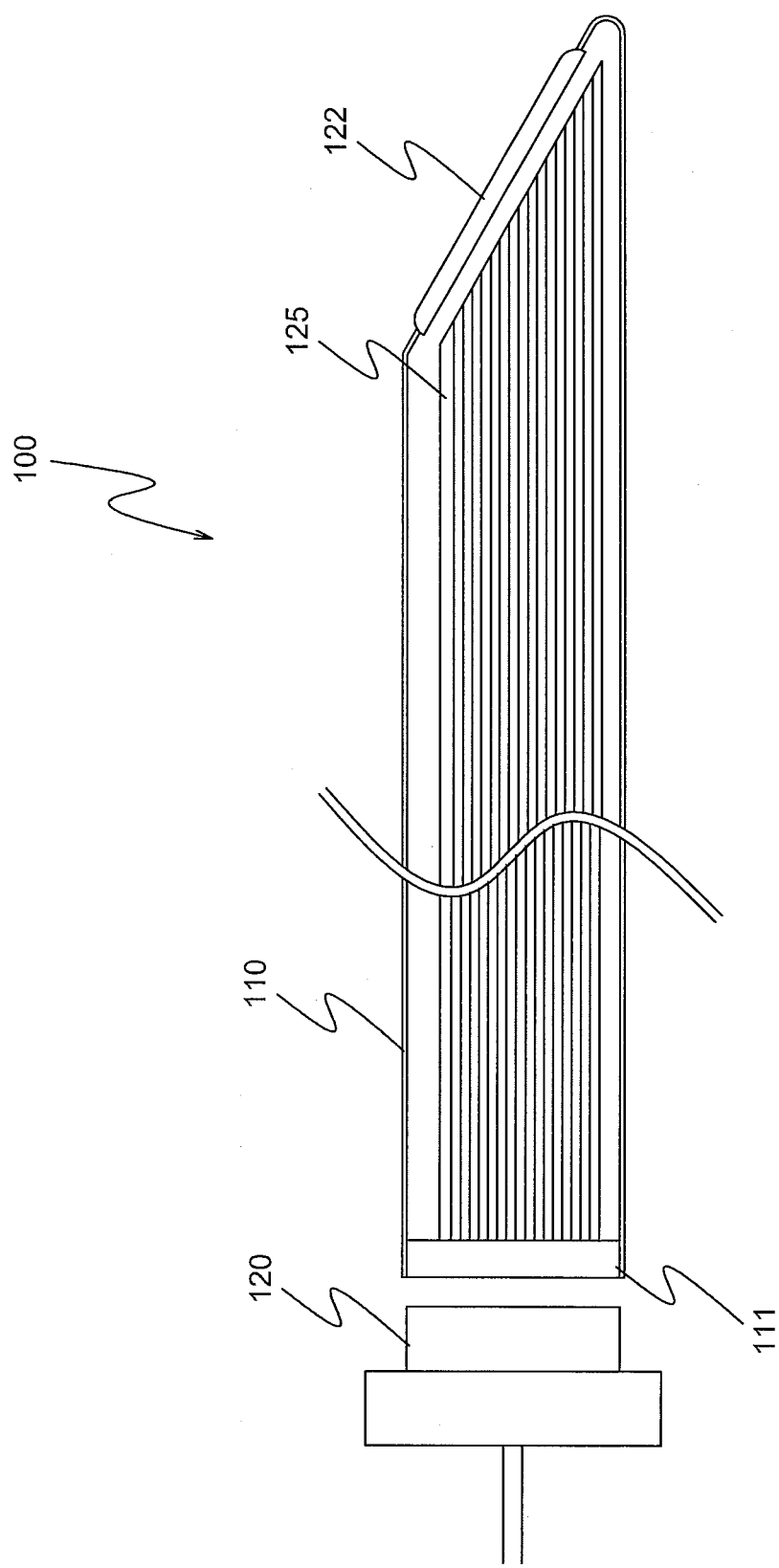
FIG. 8 illustrates a side sectional view of the distal portion of a side viewing temperature probe with a fiber bundle and end-mounted focusing lens, consistent with the present inventive concepts.

Referring now to FIG. 8, a sectional view of a side-viewing temperature probe of the present inventive concepts is illustrated comprising a distal portion configured to attach to a proximal portion. Device 100 includes shaft 110 is electromechanically attachable to sensor assembly 120 via connector 111, such that sensor 120 and all components proximal to sensor 120 may be reused. Shaft 110 and fibers 125 may be disposable, e.g. single use by one patient only or limited use, or reusable.

Sensor 120 is optically aligned with a proximal end of fibers 125 while lens 122 is arranged along the beveled distal end of fibers 125. This arrangement enables lens 122 to view to the side or forward depending upon the particular construction and positioning.

Figure 9B:
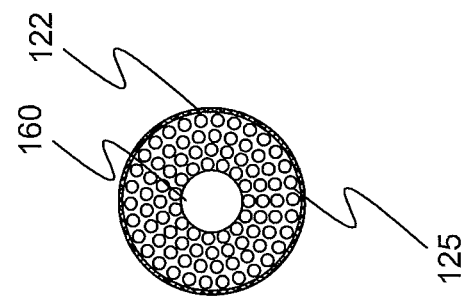
FIGS. 9A and 9B illustrate side and end sectional views, respectively, of an ablation and forward viewing temperature measurement probe including an array of optical fibers and a tip electrode, consistent with the present inventive concepts.
Figure 9A:
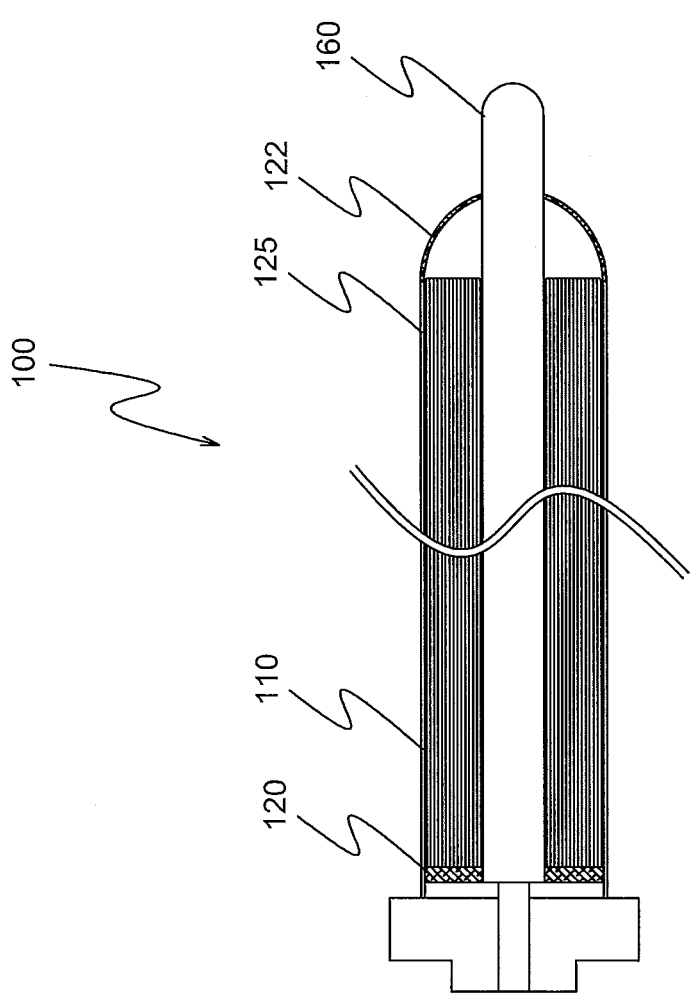

Referring now to FIGS. 9a and 9b, a side sectional and end sectional view of a forward looking RF temperature probe of the present inventive concepts is illustrated. Device 100 includes sensor 120 positioned proximal to fibers 125 and ablation element 160 at the distal end of device 100. Typically, ablation element 160 is comprised of a platinum-iridium electrode. Ablation element 160 may attach (e.g. via wires, not shown but traveling to a proximal end of device 100) to an energy generator such as an RF energy generator. Ablation element 160 is constructed and arranged to be positioned proximate tissue to be treated, such treatment including but not limited to: ablation; denaturing; excision; removal; shrinkage; and the like.

Lens 122 in combination with fibers 125 cooperate to view surrounding tissue (e.g. tissue to be ablated and tissue proximate tissue to be ablated such as tissue intended not to be damaged) so that the clinician may be alerted if target tissue has reached a desired temperature and/or the non-target tissue is not exceeding a desired temperature. For example, when ablating a tumor, if the tumor has not been entirely ablated, cancer may reoccur or spread post-procedure. This may occur when a tumor is near a blood vessel, which acts as a heat sink preventing the tumor from reaching a desired temperature.

Figure 10:
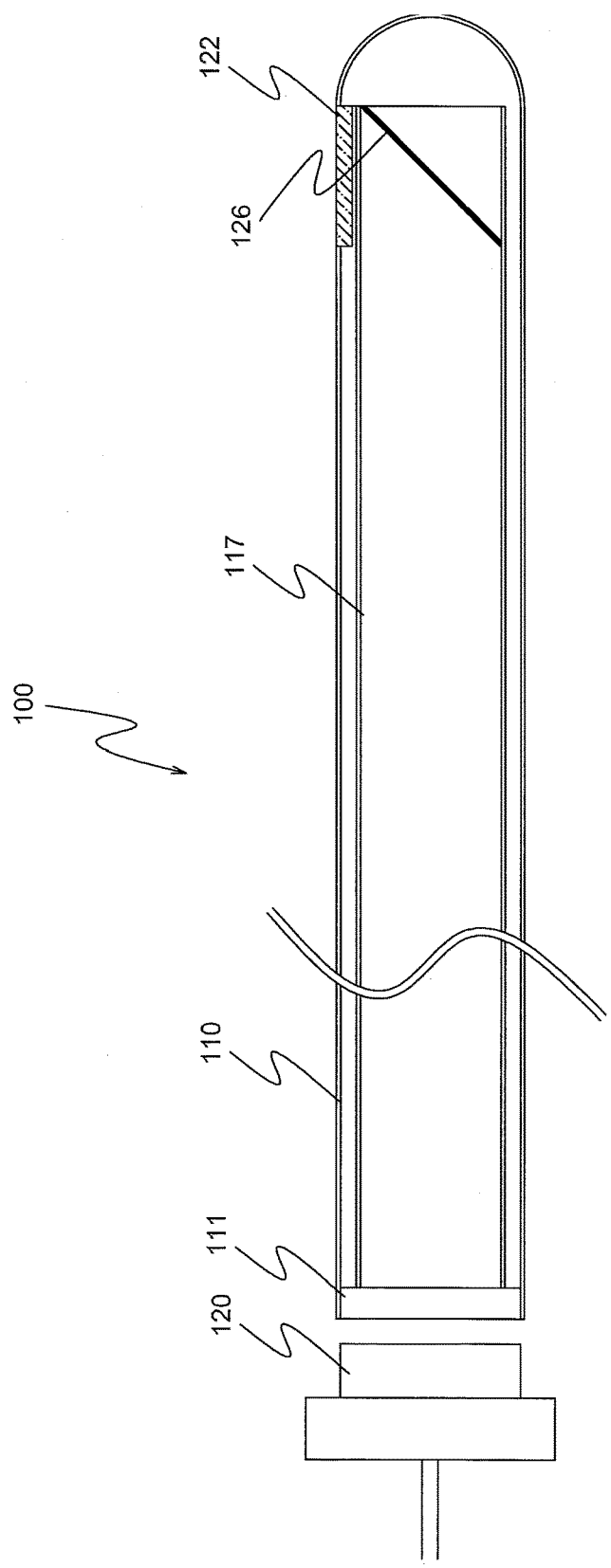
FIG. 10 illustrates a side sectional view of a side viewing temperature probe with a thermos construction, consistent with the present inventive concepts.

Referring now to FIG. 10, a sectional view of a side-viewing temperature probe of the present inventive concepts is illustrated comprising a thermos construction. The thermos construction of device 100 is achieved by creating a vacuum between shaft 110 and hollow tube 117, where hollow tube 117 is typically comprised of mirrored glass. This particular embodiment may be used to maintain hollow tube 117 in a thermally stable environment. For example, noise, such as errors and inaccuracies, may be minimized when infrared transmissions pass through lens 122 and are reflected to sensor assembly 120 via mirror 126. In addition, the thermos construction prevents the temperature of hollow tube 117 from impacting the image produced by system 10.

Mirror 126 may be configured to move in a longitudinal path or rotate by means of a movement assembly, not shown. Additionally or alternatively, device 100 may have multiple mirrors.

A partial circumferential lens 122 is positioned relative to sensor assembly 120. In an alternative embodiment, lens 122 is a full circumferential (e.g. 360°) lens, such as when sensor assembly 120 is a full 360° viewing sensor.

Additionally, this illustration includes an electromechanically attachable design via connector 111 as described in FIG. 8 hereabove. However, the device may also comprise a fixed configuration.

Figure 11:
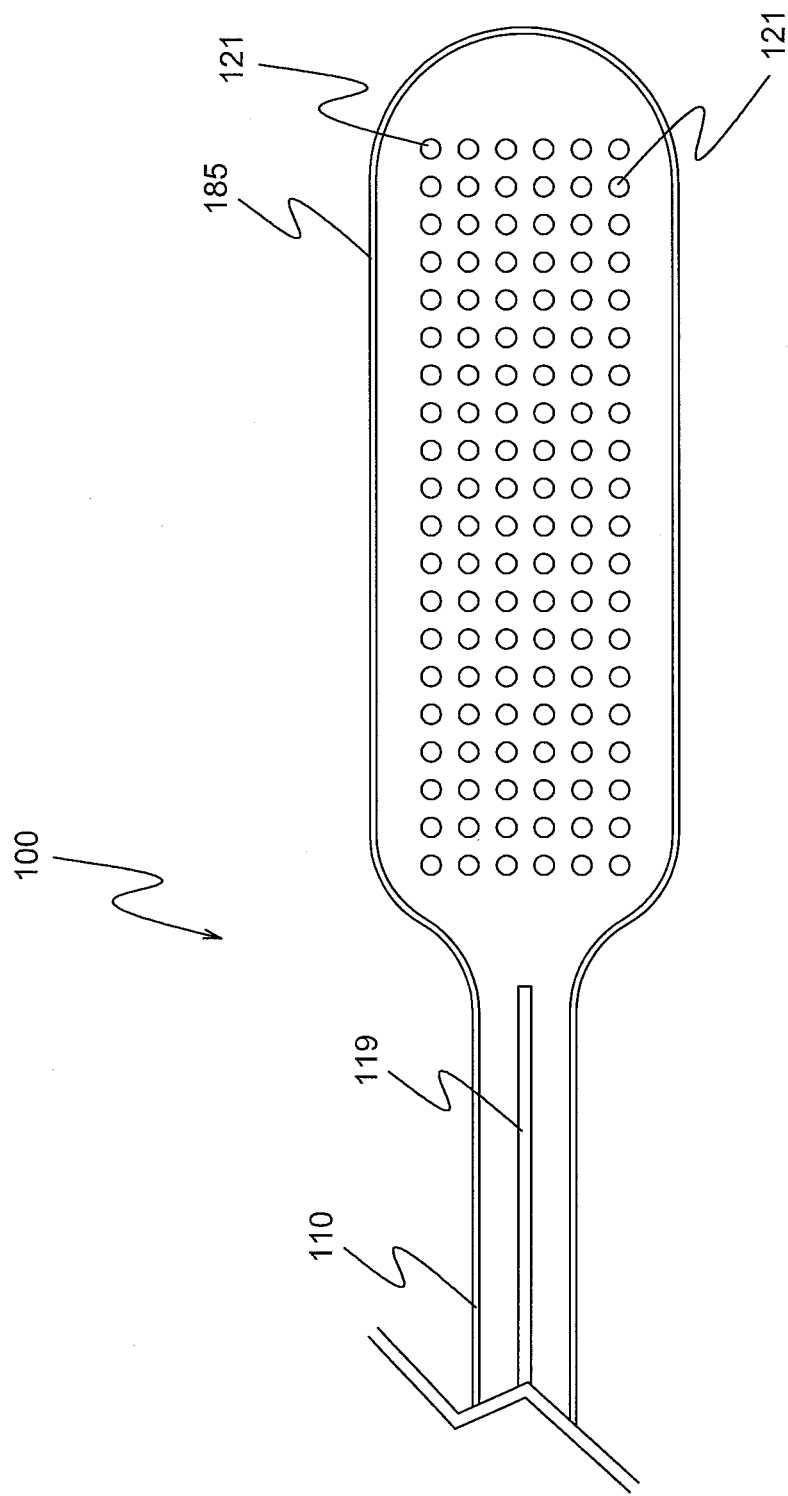
FIG. 11 illustrates a side view of a temperature probe with an array of surface sensors, consistent with the present inventive concepts.

Referring now to FIG. 11, a side-viewing temperature probe in accordance with the present inventive concepts is illustrated comprising an expandable distal portion wherein an integrated sensor array measures a patient's tissue temperature by directly contacting the tissue. Device 100 comprising a distal end of shaft 110 includes a membrane, balloon 185, which is shown in an expanded position. Balloon 185 may be hollow or may have lumens that can allow air to pass through the center of balloon 185 when expanded.

Balloon 185 includes multiple sensors 121 on its surface. In a preferred embodiment, sensors 121 are thermocouples occupying the entire surface of balloon 185. Alternatively, sensors 121 may occupy a portion of balloon 185. Typically, balloon 185 includes approximately ten sensors 121, and more typically, 100 sensors 121. In a preferred embodiment, sensors 121 are spaced substantially equidistant from one another with a separation distance of less than 0.2 mm. Alternatively, sensors 121 may be spaced less than 1.0 mm from adjacent sensor 121.

Malleable member 119 may be located on the outer surface of shaft 100 and/or embedded within the inner and outer wall of shaft 110. Malleable member 119 allows plastic deformation of the distal portion of device 100. For instance, the clinician may bend device 100 to accommodate the anatomy of the patient, e.g. patient's esophagus.

Figure 12:
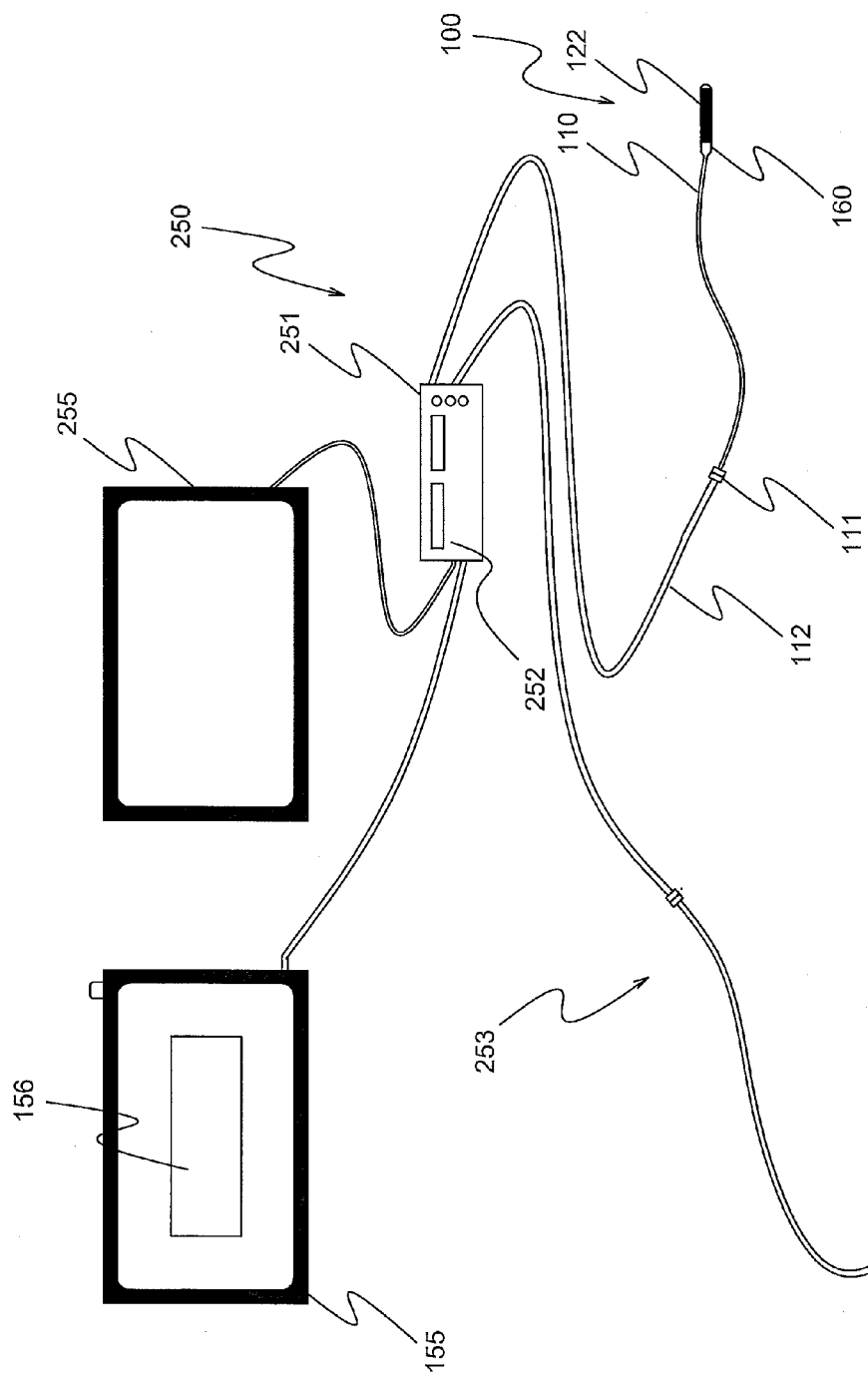
FIG. 12 illustrates a schematic view of a system including an ablation and forward viewing temperature measurement probe and an energy delivery unit, consistent with the present inventive concepts.

Referring now to FIG. 12, a schematic view of a system in accordance with the present inventive concepts where a luminal temperature measurement device is attached to an energy delivery unit demonstrating potential integration into a tissue ablation system. System 10 includes device 100 and ablation system 250.

Ablation system 250 includes ablation catheter 253 which comprises ablation elements such as electrodes, cryogenic balloons, ultrasound crystals, and the like. System 250 further includes monitor 255 which may show ablation catheter information, EKG information, energy delivery information, and other information. In addition, display 155 shows temperature map 156 information, described in FIG. 1 hereabove. Alternatively, display 155 may be integrated into monitor 155.

Ablation system 250 further comprises energy delivery unit 251 which may deliver various types of energy including: radiofrequency (RF) energy; laser energy; cryogenic energy; subsonic energy; acoustic energy; ultrasound energy; microwave energy; chemical energy; and combinations of these. Energy delivery unit 251 includes user interface 252 which may comprise one or more controls used in cooperation with device 100 and ablation catheter 253. Additionally, a signal analyzer may be integrated into unit 251 and device 100 and/or another device. User interface 252 includes adjustable controls, e.g. emergency shut-off of unit 251 and/or an alarm system, and data generated by a signal analyzer are as described in FIG. 1 hereabove.

Alternatively or additionally, all components of system 10 may include a memory storage device for recording of historic data, such as historic values of multiple patient locations, also described in FIG. 1 hereabove.

Figure 13:
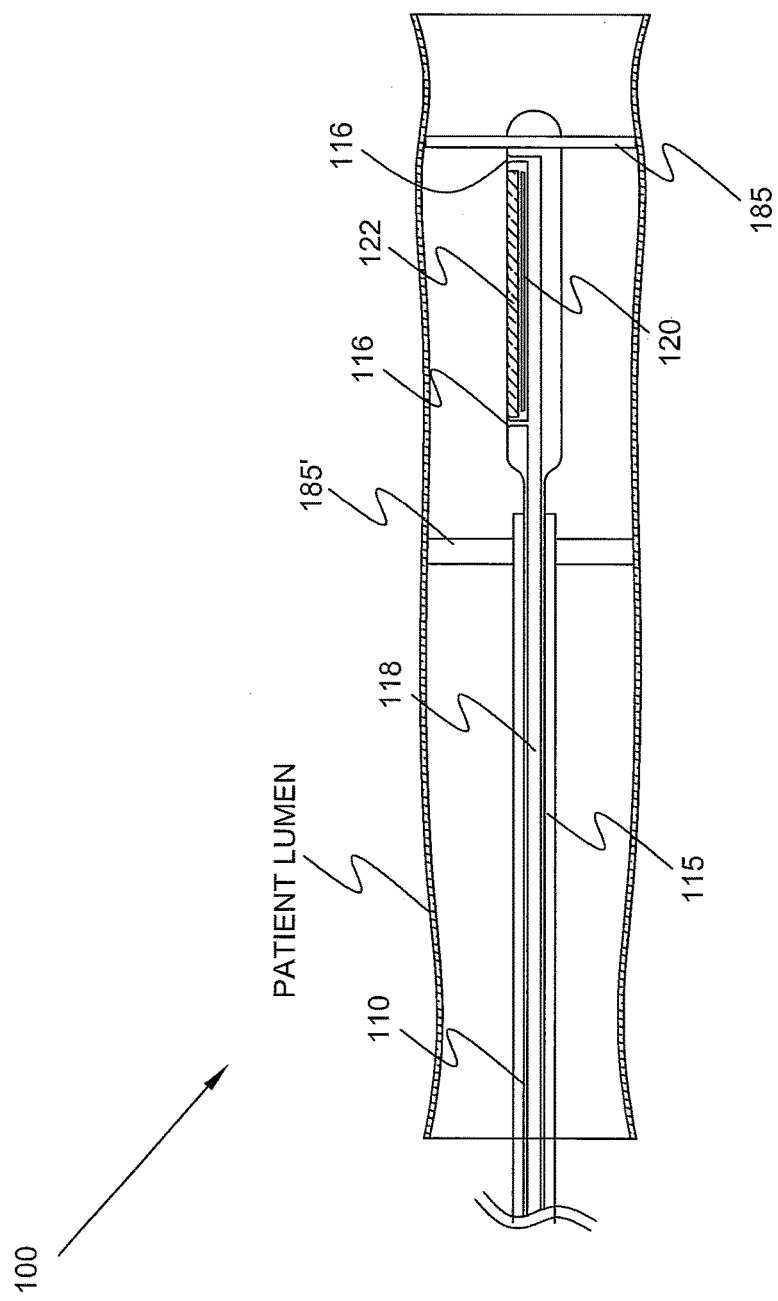
FIG. 13 illustrates a side sectional view of the distal portion of a side viewing temperature probe including positioning arms, consistent with the preset inventive concepts.

Referring now to FIG. 13, a sectional view of a side-viewing temperature probe in accordance with the present inventive concepts is shown within a body lumen of a patient, such as the esophagus, wherein the device includes an integral tissue tensioning assembly. Device 100 comprises outer sheath 115, which slidingly encloses shaft 110. Additionally, expandable cage 185 is typically positioned on a proximal portion of device 100 and configured to radially contact a patient's esophageal wall. Expandable cage 185 may be expanded upon the command of a clinician via a control mechanism, not shown.

Expandable cage 185' may be attached to outer sheath 115 such that applying force in the proximal direction tensions luminal wall tissue to create a uniform tissue surface reduce, e.g. to eliminate one or more crevices hidden within the portion of tissue and therefore outside the view of lens 122 and sensor assembly 120. Additionally or alternatively, cages 185 and/or 185' may radially tension a patient's tissue. Additionally or alternatively, cages 185 and/or 185' specifically position lens 122 and sensor assembly 120 within a lumen of a patient, e.g. the center of a lumen.

Expandable cage 185 and/or 185' may be arranged in numerous forms while remaining configured to contact a patient's tissue such that force applied between shaft 110 and outer sheath 115 tensions the tissue between cages 185 and/or 185'. For example, cages 185 and/or 185' may include a balloon, which may expand by filling with a gas such as air or a liquid, such as saline. Also, cages 185 and/or 185' may be a stent or opposing fingers, spokes or other projections. Additionally or alternatively, cages 185 and/or 185' may include a shape memory device.

In this embodiment, a partial circumferential lens 122 is positioned relative to sensor assembly 120. In an alternative embodiment, lens 122 is a full circumferential (e.g. 360°) lens, such as when sensor assembly 120 is a full 360° viewing sensor.

Device 100 includes lumen 118, which may be used to carry fluid from a proximal portion of device 100 to ports on the proximal end of device 100, such as ports 105a and/or 105b of FIG. 1. Examples of fluids include: cooling fluid, such as saline, a therapeutic drug or other agent, or combinations of these.

In an alternative embodiment, a sensor may be placed within expandable cage 185 and/or 185' to measure temperature, pressure, pH, and/or other physiologic parameters of a patient.

In yet another embodiment, outer sheath 115 and expandable cage 185' may be a separate device working in cooperation with the remaining components of device 100.

Figure 14:
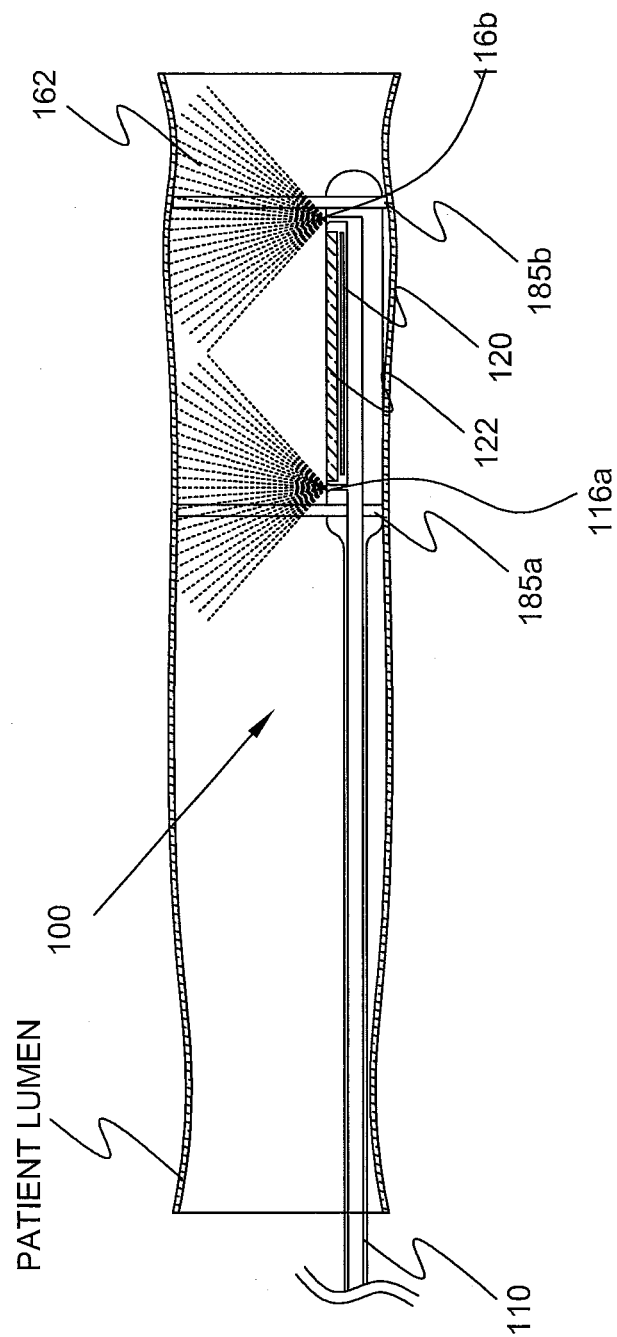
FIG. 14 illustrates a side sectional view of the distal portion of a side viewing temperature probe including fluid delivery ports, consistent with the present inventive concepts.

Referring now to FIG. 14, a sectional view of a side-viewing temperature probe in accordance with the present inventive concepts is shown within a body lumen of a patient, such as the esophagus, wherein the device has integral positioning members and fluid injection ports. Device 100 includes positioning members 185a and 185b located proximal and/or distal to lens 122. Members 185a and 185b position the distal portion of device 100 and are configured to be positioned asymmetrically within a lumen of a patient. Types of positioning members 185a and 185b are similar to those described in FIG. 13 hereabove.

Device 100 may also include a tissue temperature modifying assembly, which is configured to cool or warm multiple patient locations. An endothermic reaction will occur to cool the tissue, while an exothermic reaction will occur to warm the tissue.

Additionally or alternatively, a fluid may exit ports 116a and/or 116b to cool or warm the tissue, e.g. via heated saline. Also, a Peltier component may be included to cool or warm fluid prior to exiting ports 116a and/or 116b.

In an alternative embodiment, a separate catheter device including fluid injection ports 116a and 116b may be included on the distal portion of device 100.

Referring now to FIG. 15A, a side view of a side-viewing temperature probe in accordance with the present inventive concepts is illustrated including an outer sheath that may be advanced and/or retracted to clean the lens of the device. Device 100 includes cleaning assembly 180, a slideable sheath which fixedly surrounds shaft 110, and includes edge 181 positioned at its distal end.

Cleaning assembly 180, in cooperation with edge 181, may be used to clean debris, such as mucus, blood, or other biological material or non-biological contaminants from lens 122, such as when device 100 is placed into a body location such as the esophagus or other body lumen. Components of a sensor assembly, such as mirrors, lenses such as lens 122, and/or one or more arrays of infrared sensors, not shown but described in detail in reference to other figures included herein, may be adversely impacted by debris on lens 122 and may require at least one cleaning during use.

Cleaning assembly 180 and edge 181 perform a wiping function such as by advancing cleaning assembly 180, as shown in FIG. 15B, causing edge 180 to wipe debris from lens 122. A repeated back and forth motion may be used to clean lens 122, and one or more cleaning fluids such as saline may be delivered from a port, not shown but typically proximate edge 181 as is described in reference to FIG. 16 herebelow.

In an alternative embodiment, device 100 may include multiple cleaning assemblies 180, wherein each cleaning assembly is disposable. For example, first cleaning assembly may be utilized for a single patient and the second utilized for the same patient or a different patient.

In yet another embodiment, cleaning assembly 180 may be removable from device 100. Additionally or alternatively, cleaning assembly 180 may have a longitudinal slit 183 enabling lateral attachment to shaft 110 while shaft 110 is placed into a lumen of a patient, and one or more cleaning assemblies 180 may be laterally attached to shaft 110 one or more times during a single procedure.

Figure 16:
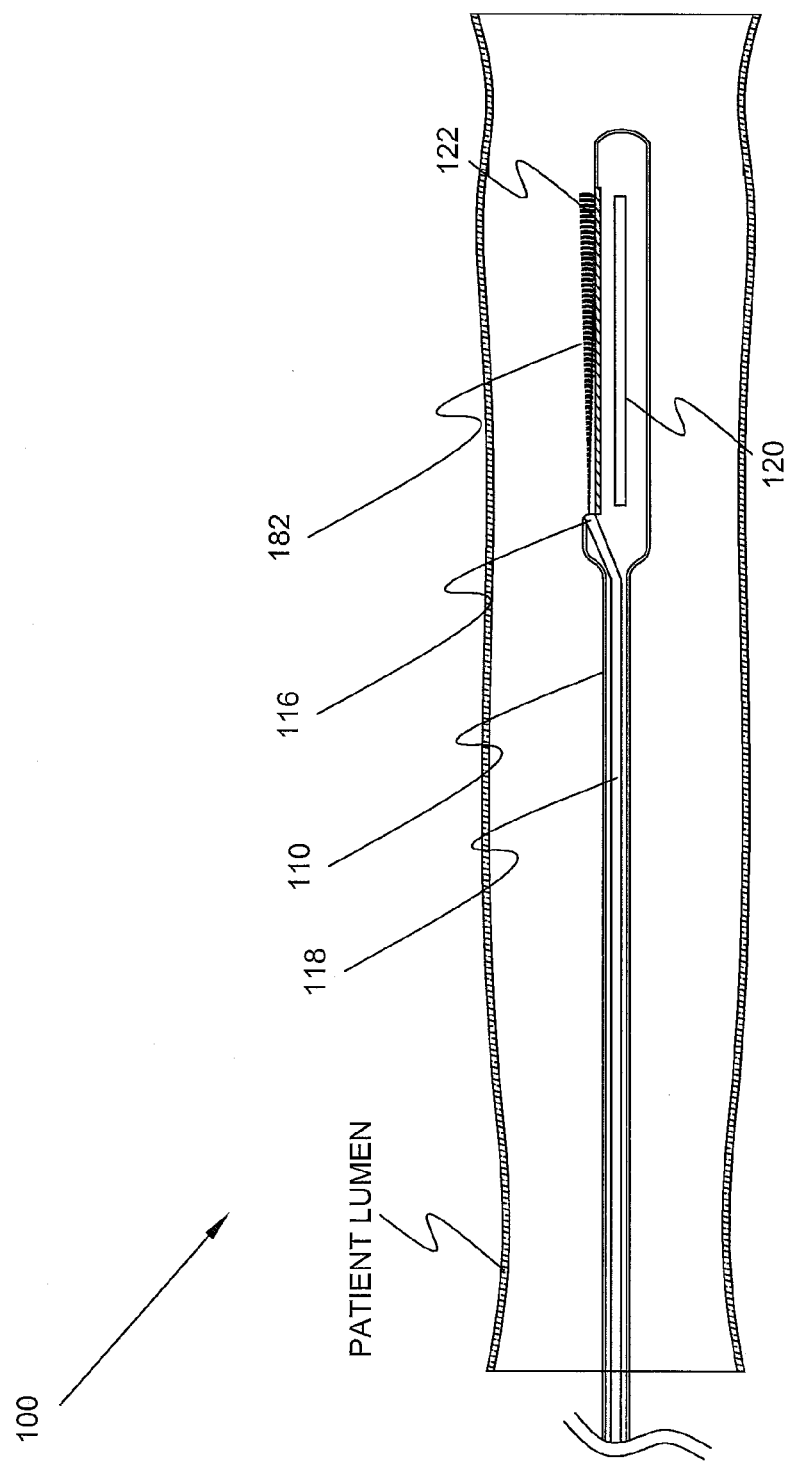
FIG. 16 illustrates a side sectional view of the distal portion of a side viewing temperature measurement probe with a cleaning fluid delivery port; consistent with the present inventive concepts.

Referring now to FIG. 16, a side sectional view of a side-viewing temperature probe in accordance with the present inventive concepts is shown within a body lumen of a patient, such as the esophagus, wherein the device includes a cleaning assembly designed to remove debris from a lens or other portion of the probe. Device 100 includes shaft 110 and sensor assembly 120 positioned in a distal portion of device 100 and configured to provide temperature information for multiple patient locations. Lumen 118 connects to a port, not shown but typically a standard luer connector, positioned on the proximal end of device 100 so that an infusion delivery device, such as a syringe or pump, dispenses cleaning medium 182 through lumen 118 and out of port 116. Port 116 may include a nozzle or other flow director such as to direct cleaning medium 182 onto lens 122 and/or another optical or other component of device 100. Cleaning medium 182 may be a liquid or gas, and is typically saline. Additionally or alternatively, cleaning medium may be saline or other biologically compatible material, and may include a cleaning agent such as a detergent. Further, cleaning medium 182 may be warmed or cooled.

Device 100 may include a second cleaning assembly. For example, a second port may be connected to lumen 118 or a different lumen, such as to clean debris from another portion of lens 122 or another portion of device 100.

Figure 17:
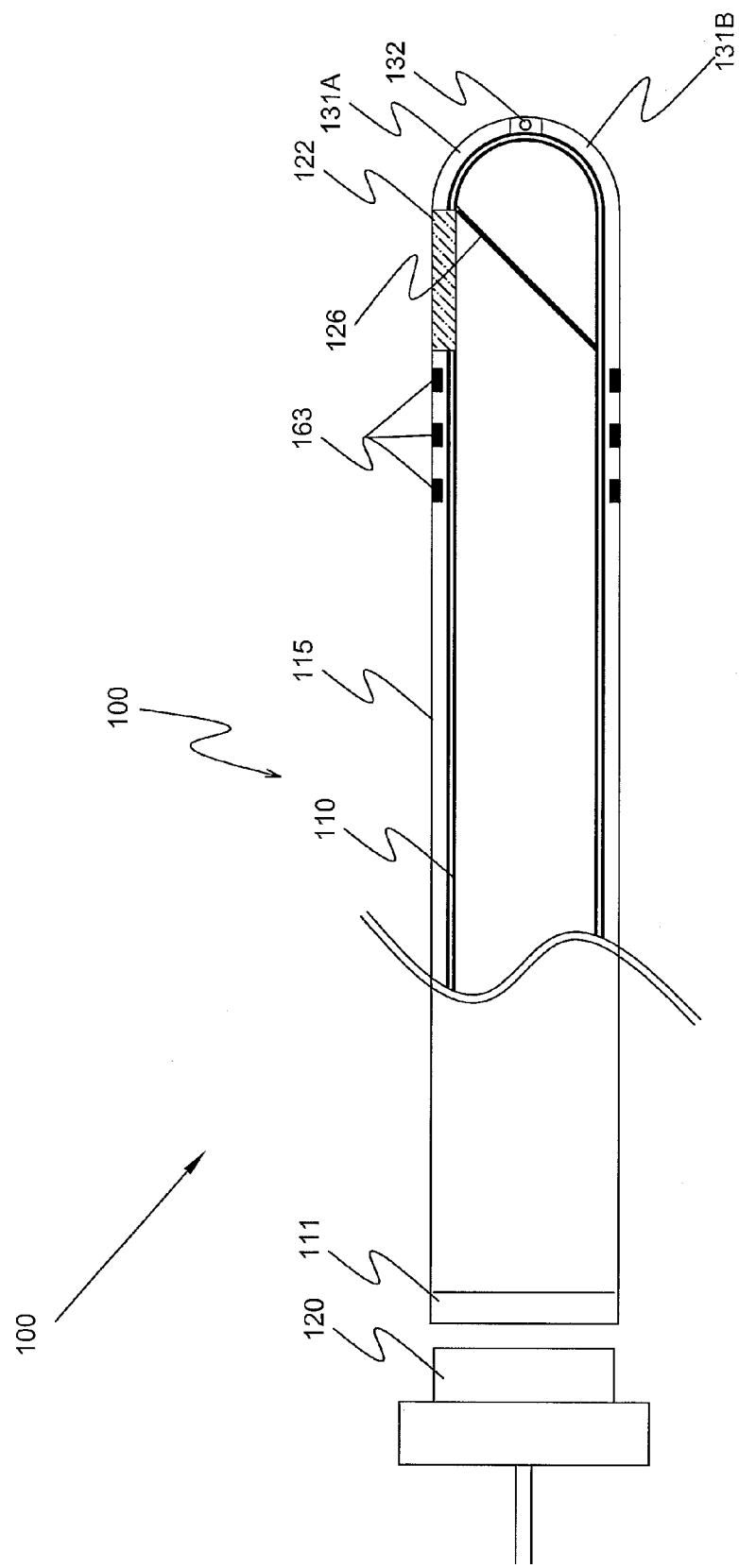
FIG. 17 illustrates a side sectional view of the distal portion of a side viewing temperature measurement probe with a detachable portion including lens, mirror, cooling chamber and sensors, consistent with the present inventive concepts.

Referring now to FIG. 17, a partial sectional side view of a side looking temperature probe in accordance with the present inventive concepts is illustrated, including an integral temperature stabilizing assembly constructed and arranged to improve the quality of the temperature map of multiple patient locations by reducing or eliminating the effect of varied or varying temperatures of one or more components of the temperature probe. Mirror 126 cooperates with lens 122 to transmit radiation (e.g. infrared radiation) through shaft 110 in a proximal direction to one or more sensor assemblies, not shown but typically located in a handle or other proximal portion of device 100, or an electronic unit connected to device 100. Mirror 126 and lens 122 may be further configured as described in FIG. 10 hereabove such that device 100 produces a temperature map of multiple patient locations.

Device 100 of FIG. 17 includes a thermos construction and a circulating fluid pathway that independently or in combination help to maintain shaft 110, mirror 126, lens 122 and/or another component or portion of a component of device 100 at a constant temperature, such as to reduce infrared radiation artifacts that reduce the quality of the temperature map produced by device 100.

Shaft 110 is positioned within outer sheath 115 in a thermos-like construction to maintain one or more components of and spaces within device 100 in a relatively isothermal condition. The outer surface of shaft 110 and/or the inner surface of outer sheath 115 may have a mirrored or other reflective surface. Shaft 110 may comprise a glass material with a mirrored surface, common to thermos devices and used to avoid heat transfer to or from shaft 110.

Alternatively or additionally, device 100 may be configured to allow a fluid to pass through space 131A and space 131B between shaft 110 and outer sheath 115 and exit thru-hole 132 at the distal end of device 100, such as to maintain shaft 110, lens 122 and/or mirror 126 in a stable, constant temperature state. Fluid may be delivered around shaft 110 such as to warm or cool shaft 110 or another component of device 100. Heating and/or cooling assemblies (e.g. Peltier components) may be used to increase, decrease and/or stabilize temperature of the fluid or a component of device 100. In one embodiment, temperature is maintained above or below body temperature.

Device 100 includes temperature sensors 163, typically ring-shaped, configured to monitor temperature of outer sheath 115, shaft 110 and/or a fluid traveling through outer sheath 115 and shaft 110. Additionally, sensors 163 may monitor the temperature of the environment in which device 100 is placed, e.g. patient tissue surrounding device 100. Sensors 163 may be used to provide temperature information fed back to the fluid delivery device or a heat exchanging device such that closed loop temperature control can be achieved. Alternatively or additionally, one or more sensors 163 may sense a parameter other than temperature, such as a sensor configured to measure a pressure, an electromagnetic condition, a physiologic parameter, or other condition.

A potential advantage of integrating a temperature stabilizing assembly within device 100 is that the performance of device 100 is improved by reducing the adverse effects of varied and varying temperatures of any component or a portion of any component of device 100, such as temperature variations within shaft 110, lens 122, mirror 126 and/or another component or portion of shaft 110.

Figure 18:
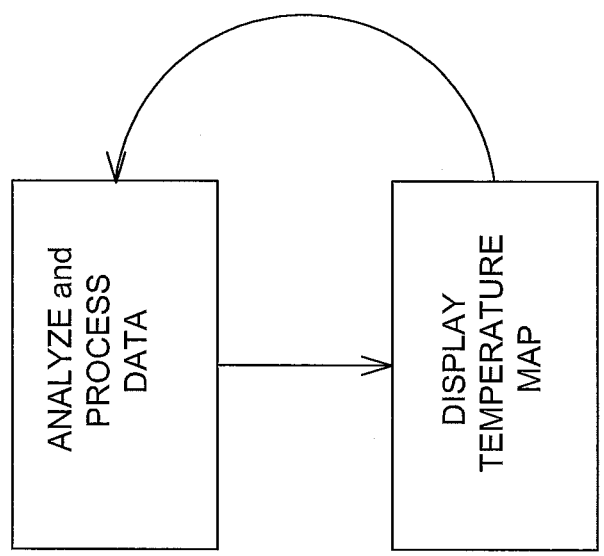
FIG. 18 illustrates a flow chart of a data analysis and processing function for a temperature measurement probe, consistent with the present inventive concepts.

Referring now to FIG. 18, a flow chart of a method for analyzing and/or processing temperature information to produce a temperature map of multiple patient locations is illustrated. In a first step, information received from a sensor assembly and/or another component or assembly of a system in accordance with the present inventive concepts is analyzed and/or processed such as via one or more image processing or other algorithms. As a result of this analysis and/or processing, a temperature map of multiple patient locations is displayed. The system comprises many features enabling the user, e.g. a clinician, to analyze temperature and other data. Numerous image stabilization algorithms may be employed, such as an image stabilization algorithm based on an accelerometer included in a temperature probe in accordance with the present inventive concepts.

The system may include manual or automatic panning and zooming functions. For example, an auto-zoom feature enables the clinician to zoom into an area where tissue temperature has increased. In one embodiment, if a temperature of an area outside the periphery of the display or along the boundary of the display increases, the display may automatically reposition and/or zoom out with or without operate input. In another embodiment, if a tissue area monitored by the device includes a temperature change that is not currently being viewed, the displayed information may automatically change such as via zooming out or repositioning at the same zoom.

An additional analytical feature of the system includes an alert detection component where the clinician may be alerted if tissue rises or falls outside a desired or expected temperature and/or outside a range of desired or expected temperatures. For example, if the desired tissue temperature is 37° C., and one or more tissue locations reach 50° C., the clinician may be alerted. Alternatively or additionally, one or more alerts may be included based on mathematical or other processing of temperature information, such as an algorithm which integrates temperature over time for one or more tissue locations.

The data analysis of the device may comprise an error checking algorithm that is configured to detect inconsistencies, such as one or more readings that are outside of one or more pre-determined boundary conditions. For example, if 10,000 data points are reading 37° C., and one data point is reading 50° C., the system will detect and alert the clinician that 50° C. is inaccurate.

As described in reference to FIG. 1, system 10 may include an alert device such as an audible transducer. An audible transducer can be configured to produce sounds that correlate to an analysis of temperatures. For example, a continuous beep may sound if the tissue temperature exceeds a desired temperature. In another example, one or more sounds represent temperature related information (e.g. processed temperature information) including but not limited to: cumulative temperature from multiple locations; average temperature; maximum temperature; temperature above a threshold; and combinations of these. The produced sound may represent one or more temperature or calculated temperature values based on one or more of: frequency; sound pattern; and volume.

Alternatively or additionally, a visible transducer may be included within the system, such as an LED. Here, a light may blink if the tissue temperature exceeds a desired temperature, or a pattern of blinking and/or light intensity may represent temperature related information.

The system may further comprise a noise reduction algorithm wherein the system may filter out known sources of noise, e.g. known infrared radiation sources.

The system may also comprise a calibration assembly, which may include a subroutine integral to a start-up or other system condition (e.g. for each new patient use). Additionally or alternatively, a calibration assembly may use a calibration standard proximate the device or within the device.

In addition to a temperature map, additional information may be processed and/or analyzed. For example, information received from a visible light sensor (e.g. a CCD camera), an ultrasound imaging device, and the like, may be analyzed and processed by the system.

In addition to displaying a temperature map, a control signal may be produced based on the analysis and/or processing of temperature information received from the sensor assembly in accordance with the present inventive concepts. In one embodiment, a feedback circuit may be included to control an energy delivery unit, e.g. an energy delivery unit used to prove ablation energy to a device positioned to ablate the heart of a patient. For example, a particular result from the data analysis may cease or modify, e.g. increase or decrease, the amount of energy delivered from an energy delivery unit. In one embodiment, the energy delivery device is unable to deliver energy to the system if it is not attached to the device or system. Additionally or alternatively, a feedback circuit may control a cooling and/or warming assembly, such as a cooling or warming assembly configured to cool or warm tissue when a measured temperature rises above or below, respectively, a threshold.

Figure 19:
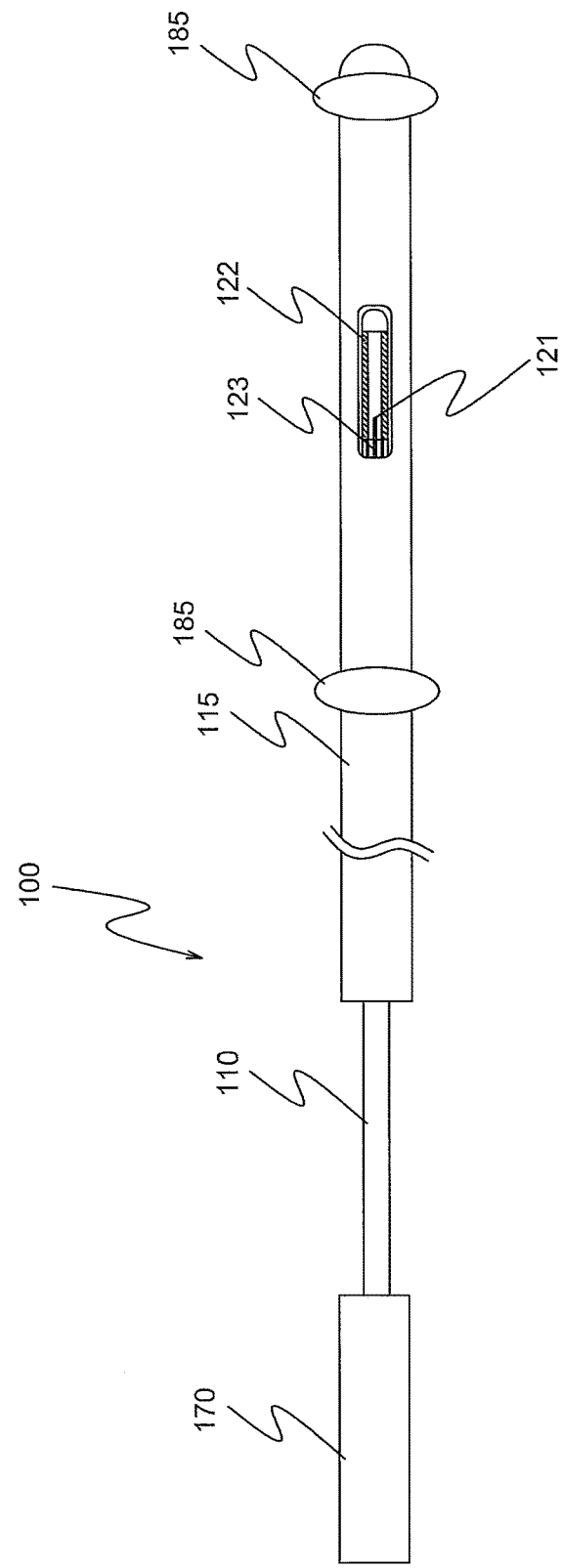
FIG. 19 illustrates a side view of the distal portion of a side viewing temperature probe with a disposable portion including an outer sheath and positioning arms, and a reusable portion including a sensor assembly.

Referring now to FIG. 19, a side view of a side-viewing temperature probe in accordance with the present inventive concepts is illustrated comprising reusable and disposable portions as well as a sensor mounted to a rotatable drive shaft. Device 100 includes sensor 121 which is constructed and arranged to provide temperature information such that a temperature map of multiple patient locations can be displayed. Sensor 121 is fixedly mounted to a distal end of drive shaft 123 which travels proximally through shaft 110. Drive shaft 123 may be an optical fiber, such as when sensor 121 is a modified end to a fiber and/or a lens or mirror attached to the end of a fiber. Drive shaft 123 may include one or more wires such as when sensor 121 is an electronic assembly which transmits information down a wire of drive shaft 123. Lens 122 is positioned at a longitudinal location on outer sheath 115 that is proximate sensor 121.

In one embodiment, drive shaft 123 rotates sensor 121 enabling sensor 121 to view through a partial circumferential lens 122, e.g. a lens covering 90° or 180° of the circumference of sheath 115. The rotation of sensor 121 may be continuous in a circular path, i.e. spin past the partial circumference of the lens 122, leaving a void in the viewing window. Alternatively, the rotation of sensor 121 may be reciprocating, i.e. in a back and forth motion to maintain view within the partial circumference of lens 122, such as to translate over a distance of at least 1 mm, typically between 10 mm and 80 mm, more typically at least 20 mm. Alternatively, lens 122 is wider, e.g. 360°, and sensor 121 would have continuous viewing capabilities as sensor 121 is rotated continuously by shaft 121.

In a typical embodiment, linear drive assembly 170 is operably connected to shaft 123, which rotates and moves axially in a forward and back motion; this technology is currently used in intravascular ultrasound 3-D imaging products. In this particular embodiment, sensor 121 is capable of viewing through substantially all of the surface area of lens 122.

In a particular embodiment, device 100 includes positioning members 185, as discussed in FIG. 13 hereabove, and outer sheath 115, which are typically supplied sterile, while linear drive assembly 170 and shaft 110 may be non-sterile. Alternatively or additionally, positioning members 185 and outer sheath 115 may be disposable, e.g. single use by one patient only or limited use, while linear drive assembly 170 and shaft 110 may be utilized for multiple patient procedures.

While the preferred embodiments of the devices and methods have been described in reference to the environment in which they were developed, they are merely illustrative of the principles of the inventive concepts. Modification or combinations of the above-described assemblies, other embodiments, configurations, and methods for carrying out the inventive concepts, and variations of aspects of the inventive concepts that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A temperature measurement probe for a patient, comprising:
    an elongate member comprising a proximal portion and a distal portion;
    a sensor assembly comprising a first portion and a second portion, the first portion positioned in the elongate member distal portion, the first portion constructed and arranged to direct infrared signals from a tissue surface of the patient to the second portion, and the first portion further constructed and arranged to rotate and translate, the second portion comprising an infrared sensor that receives and processes exclusively the infrared signals, converts the received infrared signals into electrical signals, and outputs the converted electrical signals;
    a transmission conduit including one and only one infrared fiber in the elongate member that is optically connected between the first portion and the second portion, that is constructed and arranged to rotate and translate relative to the elongate member, and that transmits from the first portion to the infrared sensor of the second portion only the infrared signals received from a length of the tissue surface;
    wherein the probe is constructed and arranged to produce in response to the electrical signals converted from the infrared signals temperature information for generating a temperature map for multiple patient locations of the tissue surface positioned about the elongate member distal portion, wherein the temperature information corresponding to the multiple patient locations and converted from the infrared signals received by the rotating and translating transmission conduit is combined to generate the temperature map, and wherein the first portion of the sensor assembly rotates and translates in the reciprocating repetitive back and forth motion to update the temperature map.

2. The probe of claim 1 further comprising a drive assembly that translates the first portion in a reciprocating repetitive periodic back and forth motion for receiving at the first portion the infrared signals.

3. The probe of claim 2 wherein the drive assembly comprises a drive shaft.

4. The probe of claim 2, wherein the first portion of the sensor assembly passes a tissue surface at a same patient location of the multiple patient locations during the reciprocating repetitive periodic back and forth motion of the first portion, and wherein infrared signals are received by the first portion from the tissue surface at the same patient location for each pass in the reciprocating repetitive periodic back and forth motion of the first portion.

5. The probe of claim 4, wherein the probe determines whether a temperature change occurs at the tissue surface of the same patient location.

6. The probe of claim 5, wherein the infrared signals of the tissue surface at the same patient location are received corresponding to a range of temperatures over time.

7. The probe of claim 1 wherein the first portion is further constructed and arranged to rotate continuously.

8. The probe of claim 1 wherein the first portion comprises at least one of a prism or a lens only at the elongate member distal portion.

9. The probe of claim 1 wherein the first portion comprises an element selected from the group consisting of: lens; mirror; filter; fiber optic cable; prism; amplifier; refractor; splitter; polarizer; and combinations thereof.

10. The probe of claim 1 wherein the transmission conduit comprises an infrared transparent fiber optic.

11. The probe of claim 1 wherein the transmission conduit is constructed and arranged to rotate and translate.

12. The probe of claim 1 wherein the one and only one infrared fiber of the transmission conduit is constructed and arranged to translate in a reciprocating motion.

13. The probe of claim 1 wherein the transmission conduit is constructed and arranged to rotate continuously.

14. The probe of claim 1 wherein the second portion is positioned proximal to the elongate member proximal portion.

15. The probe of claim 1 further comprising a functional element positioned at least one of in or on the elongate member distal portion.

16. The probe of claim 15 wherein the functional element comprises a temperature sensor.

17. The probe of claim 16 wherein the temperature sensor is constructed and arranged to calibrate the probe.

18. The probe of claim 1 wherein the elongate member comprises a lens surrounding the first portion.

19. The probe of claim 1, wherein the probe is further constructed and arranged to update the temperature map.

20. The probe of claim 1, wherein the sensor assembly includes a material selected from the group consisting of: germanium; arsenic; selenium; sulfur; tellurium; silver halide; or other material that reduces impedance or provides zero impedance with respect to a transmission of infrared light.

21. The probe of claim 1, wherein the infrared sensor includes one and only one infrared sensor constructed and arranged to receive the infrared signals from the one and only one infrared fiber.

22. The probe of claim 1, wherein the received infrared signals represent a transmission of infrared light collected from multiple locations of the tissue surface as determined by the translation and rotation of the one and only one infrared fiber.

23. A method of producing a temperature map, comprising:
    selecting a temperature measurement probe comprising:
        an elongate member comprising a proximal portion and a distal portion;
        a sensor assembly comprising a first portion and a second portion, the first portion positioned in the elongate member distal portion, the first portion constructed and arranged to direct infrared signals from a tissue surface of a patient to the second portion, and the first portion further constructed and arranged to rotate and translate, the second portion comprising an infrared sensor that receives and processes exclusively the infrared signals, converts the received infrared signals into electrical signals, and outputs the converted electrical signals;

a transmission conduit optically having one and only one infrared fiber in the elongate member that is connected between the first portion and the second portion, that is constructed and arranged to rotate and translate relative to the elongate member, and that transmits from the first portion to an infrared sensor of the second portion only the infrared signals received from the tissue surface;

positioning the elongate member distal portion in a body cavity of a patient; and producing in response to the electrical signals converted from the infrared signals temperature information for generating a temperature map for multiple patient locations positioned about the elongate member distal portion, wherein the temperature information corresponding to the multiple patient locations and converted from the infrared signals received by the rotating and translating transmission conduit is combined to generate the temperature map, and wherein the first portion of the sensor assembly rotates and translates in the reciprocating repetitive back and forth motion to update the temperature map.

24. The method of claim 23 further comprising performing a calibration of the sensor assembly.

25. The method of claim 24 wherein the probe further comprises a temperature sensor positioned in the elongate member distal portion, wherein the calibration is performed based on signals produced by the temperature sensor.

26. The method of claim 25 further comprising performing a cardiac ablation procedure based on the temperature map.

27. The method of claim 26 wherein the cardiac ablation procedure is performed to treat atrial fibrillation.

28. The method of claim 23, further comprising updating the temperature map during positioning of the elongate member distal portion in the body cavity of the patient.

29. The method of claim 23, wherein the first portion of the sensor assembly passes a tissue surface at a same patient location of the multiple patient locations during a reciprocating repetitive periodic back and forth motion of the first portion, and wherein infrared signals are received by the first portion from the tissue surface at the same patient location for each pass in the reciprocating repetitive periodic back and forth motion of the first portion.

30. The method of claim 29, wherein the probe determines whether a temperature change occurs at the tissue surface of the same patient location.

31. The method of claim 29, wherein the infrared signals of the tissue surface at the same patient location are received corresponding to a range of temperatures over time.

\* \* \* \* \*